United States Patent
Nofzinger

(10) Patent No.: US 10,610,661 B2
(45) Date of Patent: Apr. 7, 2020

(54) NONINVASIVE, REGIONAL BRAIN THERMAL STIMULI FOR THE TREATMENT OF MIGRAINE

(71) Applicant: University of Pittsburgh—Of the Commonwealth System of Higher Education, Pittsburgh, PA (US)

(72) Inventor: Eric A. Nofzinger, Allison Park, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/386,145

(22) Filed: Apr. 16, 2019

(65) Prior Publication Data

US 2019/0275287 A1    Sep. 12, 2019

Related U.S. Application Data

(63) Continuation-in-part of application No. 15/921,528, filed on Mar. 14, 2018, which is a
(Continued)

(51) Int. Cl.
*A61M 21/02* (2006.01)
*A61M 21/00* (2006.01)
(Continued)

(52) U.S. Cl.
CPC ........... *A61M 21/02* (2013.01); *A61F 7/0085* (2013.01); *A61F 7/10* (2013.01); *A61M 19/00* (2013.01);
(Continued)

(58) Field of Classification Search
CPC ........... A61M 21/02; A61M 2021/0066; A61F 2007/0056
See application file for complete search history.

(56) References Cited

U.S. PATENT DOCUMENTS 222,690 A    12/1879   Goldschmidt
301,931 A    7/1884    Smith et al.
(Continued)

FOREIGN PATENT DOCUMENTS

EP    1977710    10/2008
EP    2359781    8/2011
(Continued)

OTHER PUBLICATIONS

Adam et al.; Physiological and psychological differences between good and poor sleepers; J. psychiat. Res.; 20(4); pp. 301-316; Jan. 1986.
(Continued)

*Primary Examiner* — Kaitlyn E Smith
(74) *Attorney, Agent, or Firm* — Shay Glenn LLP

(57) ABSTRACT

Methods, systems and devices for treating headaches, including migraines. In some variations these methods may include enhancing sleep, including enhancing the quality of sleep, reducing sleep onset time, increasing total sleep time, treating insomnia, and/or treating other neurological disorders by non-invasive temperature regulation of the frontal cortex prior to and/or during sleep.

20 Claims, 21 Drawing Sheets

Related U.S. Application Data continuation-in-part of application No. 14/435,515, filed as application No. PCT/US2013/070251 on Nov. 15, 2013, now abandoned, said application No. 15/921,528 is a continuation-in-part of application No. 15/597,057, filed on May 16, 2017, which is a continuation-in-part of application No. 14/749,590, filed on Jun. 24, 2015, now Pat. No. 9,669,185, which is a continuation of application No. 13/868,015, filed on Apr. 22, 2013, now Pat. No. 9,089,400, which is a continuation of application No. 13/019,477, filed on Feb. 2, 2011, now Pat. No. 8,425,583, which is a continuation-in-part of application No. 11/788,694, filed on Apr. 20, 2007, now Pat. No. 8,236,038, said application No. 13/019,477 is a continuation-in-part of application No. 12/288,417, filed on Oct. 20, 2008, now Pat. No. 9,492,313.

(60) Provisional application No. 60/793,680, filed on Apr. 20, 2006, provisional application No. 61/727,054, filed on Nov. 15, 2012, provisional application No. 61/859,161, filed on Jul. 26, 2013, provisional application No. 61/300,768, filed on Feb. 2, 2010.

(51) Int. Cl.
| | |
|---|---|
| *A61F 7/10* | (2006.01) |
| *A61F 7/00* | (2006.01) |
| *A61B 17/00* | (2006.01) |
| *A61F 7/02* | (2006.01) |
| *A61M 19/00* | (2006.01) |

(52) U.S. Cl.
CPC ... *A61M 21/00* (2013.01); *A61B 2017/00132* (2013.01); *A61F 7/007* (2013.01); *A61F 2007/0002* (2013.01); *A61F 2007/0007* (2013.01); *A61F 2007/0056* (2013.01); *A61F 2007/0075* (2013.01); *A61F 2007/0095* (2013.01); *A61F 2007/023* (2013.01); *A61F 2007/0249* (2013.01); *A61F 2007/0292* (2013.01); *A61M 2021/0066* (2013.01); *A61M 2021/0083* (2013.01); *A61M 2205/3606* (2013.01); *A61M 2205/3626* (2013.01); *A61M 2209/088* (2013.01); *A61M 2210/06* (2013.01); *A61M 2210/0693* (2013.01)

(56) References Cited

U.S. PATENT DOCUMENTS

| | | | |
|---|---|---|---|
| 683,991 A | 10/1901 | Rowe | |
| 737,473 A | 8/1903 | Porter | |
| 805,371 A | 11/1905 | Meinecke et al. | |
| 919,614 A | 4/1909 | Meinecke | |
| 1,002,021 A | 8/1911 | Barnes | |
| 1,127,221 A | 2/1915 | Finkelstein | |
| 1,318,411 A | 10/1919 | Rozene | |
| 1,322,984 A | 11/1919 | Wesley | |
| 1,345,906 A | 7/1920 | Augustine | |
| 1,511,775 A | 10/1924 | Frederic et al. | |
| 1,522,295 A | 1/1925 | Gee | |
| 1,567,931 A | 12/1925 | Epler | |
| 1,743,244 A | 1/1930 | Shulman | |
| 1,769,186 A | 7/1930 | Morris | |
| 1,870,143 A | 8/1932 | Roux | |
| 1,964,655 A | 6/1934 | Williamson | |
| 2,049,723 A | 8/1936 | Pomeranz | |
| 2,158,571 A | 5/1939 | Culp | |
| 2,320,467 A | 6/1943 | Rabil | |
| 2,726,658 A * | 12/1955 | Chessey | F25D 17/02 |
| | | | 607/104 |
| 3,244,210 A | 4/1966 | Giacomo | |
| 3,463,161 A | 8/1969 | Andrassy | |
| 3,587,577 A | 6/1971 | Smirnov et al. | |
| 3,696,814 A | 10/1972 | Umemoto | |
| 3,717,145 A | 2/1973 | Berndt et al. | |
| 3,895,638 A | 7/1975 | Ito | |
| 3,908,655 A | 9/1975 | Lund | |
| 3,979,345 A | 9/1976 | Yates et al. | |
| 3,988,568 A | 10/1976 | Mantell | |
| 4,118,946 A | 10/1978 | Tubin | |
| 4,172,495 A | 10/1979 | Zebuhr et al. | |
| 4,204,543 A | 5/1980 | Henderson | |
| 4,356,709 A | 11/1982 | Alexander | |
| 4,425,916 A | 1/1984 | Bowen | |
| 4,466,439 A | 8/1984 | Moore | |
| 4,483,021 A | 11/1984 | McCall | |
| 4,566,455 A | 1/1986 | Kramer | |
| 4,574,411 A | 3/1986 | Yagi | |
| 4,691,762 A | 9/1987 | Elkins et al. | |
| 4,742,827 A | 5/1988 | Lipton | |
| 4,753,242 A | 6/1988 | Saggers | |
| 4,765,338 A | 8/1988 | Turner et al. | |
| 4,781,193 A * | 11/1988 | Pagden | A61F 7/007 |
| | | | 607/104 |
| 4,844,072 A * | 7/1989 | French | A61F 7/02 |
| | | | 607/104 |
| 4,854,319 A | 8/1989 | Tobin | |
| 4,891,501 A | 1/1990 | Lipton | |
| 4,920,963 A | 5/1990 | Brader | |
| 4,961,422 A | 10/1990 | Marchosky et al. | |
| 5,097,828 A | 3/1992 | Deutsch | |
| 5,097,829 A | 3/1992 | Quisenberry | |
| 5,163,425 A | 11/1992 | Nambu et al. | |
| 5,183,058 A | 2/1993 | Janese | |
| 5,184,613 A | 2/1993 | Mintz | |
| 5,197,466 A | 3/1993 | Marchosky et al. | |
| 5,228,431 A | 7/1993 | Giarretto | |
| 5,261,399 A | 11/1993 | Klatz et al. | |
| 5,274,865 A | 1/1994 | Takehashi | |
| 5,292,347 A | 3/1994 | Pompei | |
| 5,305,470 A | 4/1994 | Mckay | |
| 5,305,471 A | 4/1994 | Steele et al. | |
| 5,314,456 A | 5/1994 | Cohen | |
| 5,327,585 A | 7/1994 | Karlan | |
| 5,342,411 A | 8/1994 | Maxted et al. | |
| 5,344,437 A | 9/1994 | Pistay | |
| 5,356,426 A | 10/1994 | Delk et al. | |
| 5,400,617 A | 3/1995 | Ragonesi et al. | |
| 5,409,500 A | 4/1995 | Dyrek | |
| 5,441,476 A | 8/1995 | Kitado et al. | |
| 5,469,579 A | 11/1995 | Tremblay et al. | |
| 5,531,777 A | 7/1996 | Goldstein et al. | |
| 5,545,199 A | 8/1996 | Hudson | |
| 5,603,728 A | 2/1997 | Pachys | |
| 5,609,619 A | 3/1997 | Pompei | |
| 5,643,336 A * | 7/1997 | Lopez-Claros | A61F 7/02 |
| | | | 126/204 |
| 5,658,324 A | 8/1997 | Bailey, Sr. et al. | |
| 5,715,533 A | 2/1998 | Stein | |
| 5,755,756 A | 5/1998 | Freedman, Jr. et al. | |
| 5,837,002 A | 11/1998 | Augustine et al. | |
| 5,848,981 A | 12/1998 | Herbranson | |
| 5,867,999 A | 2/1999 | Bratton et al. | |
| 5,871,526 A | 2/1999 | Gibbs et al. | |
| 5,895,418 A | 4/1999 | Saringer | |
| 5,897,581 A | 4/1999 | Fronda et al. | |
| 5,897,582 A | 4/1999 | Agnatovech et al. | |
| 5,916,242 A | 6/1999 | Schwartz | |
| 5,948,012 A | 9/1999 | Mahaffey et al. | |
| 5,950,234 A | 9/1999 | Leong et al. | |
| 5,957,963 A | 9/1999 | Dobak, III | |
| 5,957,964 A | 9/1999 | Ceravolo | |
| 6,010,528 A | 1/2000 | Augustine et al. | |
| 6,017,337 A | 1/2000 | Pira | |
| 6,030,412 A | 2/2000 | Klatz et al. | |
| 6,051,019 A | 4/2000 | Dobak, III | |
| 6,083,254 A | 7/2000 | Evans | |
| 6,113,626 A | 9/2000 | Clifton et al. | |
| 6,126,680 A | 10/2000 | Wass | |
| 6,156,057 A | 12/2000 | Fox | |

(56) References Cited

U.S. PATENT DOCUMENTS

| | | | |
|---|---|---|---|
| 6,156,059 A | 12/2000 | Olofsson | |
| 6,183,501 B1 | 2/2001 | Latham | |
| 6,197,045 B1 | 3/2001 | Carson | |
| 6,228,376 B1 | 5/2001 | Misumi et al. | |
| 6,230,501 B1 * | 5/2001 | Bailey, Sr. | A43B 1/0054 62/51.1 |
| 6,231,595 B1 | 5/2001 | Dobak, III | |
| 6,248,126 B1 | 6/2001 | Lesser et al. | |
| 6,277,143 B1 | 8/2001 | Klatz et al. | |
| 6,295,819 B1 | 10/2001 | Mathiprakasam et al. | |
| 6,312,453 B1 | 11/2001 | Stefanile et al. | |
| 6,363,285 B1 | 3/2002 | Wey | |
| 6,375,673 B1 | 4/2002 | Clifton et al. | |
| 6,375,674 B1 | 4/2002 | Carson | |
| 6,409,746 B1 | 6/2002 | Igaki et al. | |
| 6,416,532 B1 | 7/2002 | Fallik | |
| 6,461,379 B1 | 10/2002 | Carson et al. | |
| 6,500,201 B1 | 12/2002 | Tsuchiya et al. | |
| 6,511,502 B2 | 1/2003 | Fletcher | |
| 6,516,624 B1 | 2/2003 | Ichigaya | |
| 6,523,354 B1 | 2/2003 | Tolbert | |
| 6,551,347 B1 | 4/2003 | Elkins | |
| 6,554,787 B1 | 4/2003 | Griffin et al. | |
| 6,581,400 B2 | 6/2003 | Augustine et al. | |
| 6,599,312 B2 | 7/2003 | Dobak, III | |
| 6,610,084 B1 | 8/2003 | Torres | |
| 6,629,990 B2 | 10/2003 | Putz et al. | |
| 6,669,715 B2 | 12/2003 | Hoglund et al. | |
| 6,673,098 B1 | 1/2004 | Machold et al. | |
| 6,682,552 B2 | 1/2004 | Ramsden et al. | |
| 6,692,518 B2 | 2/2004 | Carson | |
| 6,699,267 B2 | 3/2004 | Voorhees et al. | |
| 6,736,837 B2 | 5/2004 | Fox | |
| 6,740,109 B2 | 5/2004 | Dobak, III | |
| 6,740,110 B2 | 5/2004 | Babcock | |
| 6,770,085 B1 | 8/2004 | Munson | |
| 6,845,520 B2 | 1/2005 | Kim | |
| 6,854,128 B1 | 2/2005 | Faulk | |
| 6,881,219 B1 | 4/2005 | Agarwal et al. | |
| 6,921,374 B2 | 7/2005 | Augustine | |
| 6,929,656 B1 | 8/2005 | Lennox | |
| 6,962,600 B2 | 11/2005 | Lennox et al. | |
| 6,979,345 B2 | 12/2005 | Werneth | |
| 7,008,445 B2 | 3/2006 | Lennox | |
| 7,044,960 B2 | 5/2006 | Voorhees et al. | |
| 7,052,509 B2 | 5/2006 | Lennox et al. | |
| 7,056,334 B2 | 6/2006 | Lennox | |
| 7,077,858 B2 | 7/2006 | Fletcher et al. | |
| 7,087,075 B2 | 8/2006 | Briscoe et al. | |
| 7,146,211 B2 | 12/2006 | Frei et al. | |
| 7,152,412 B2 | 12/2006 | Harvie | |
| 7,179,280 B2 | 2/2007 | Mills | |
| 7,182,777 B2 | 2/2007 | Mills | |
| 7,189,252 B2 | 3/2007 | Krueger | |
| 7,229,468 B2 | 6/2007 | Wong, Jr. et al. | |
| 7,309,348 B2 | 12/2007 | Streeter et al. | |
| 7,559,907 B2 | 7/2009 | Krempel et al. | |
| 7,637,931 B2 | 12/2009 | Heaton | |
| 7,744,640 B1 | 6/2010 | Faries, Jr. et al. | |
| 7,854,754 B2 | 12/2010 | Ting et al. | |
| 7,875,066 B2 | 1/2011 | Cohen et al. | |
| 7,877,827 B2 | 2/2011 | Marquette et al. | |
| 7,909,861 B2 | 3/2011 | Balachandran et al. | |
| 7,930,772 B2 * | 4/2011 | Fontanez | A42C 5/04 2/425 |
| 8,052,624 B2 | 11/2011 | Buchanan et al. | |
| 8,226,698 B2 * | 7/2012 | Edelman | A61F 7/02 607/104 |
| 8,236,038 B2 | 8/2012 | Nofzinger | |
| 8,425,583 B2 | 4/2013 | Nofzinger | |
| 9,089,400 B2 | 7/2015 | Nofzinger | |
| 9,211,212 B2 | 12/2015 | Nofzinger et al. | |
| 9,492,313 B2 | 11/2016 | Nofzinger | |
| 9,669,185 B2 | 6/2017 | Nofzinger | |
| 10,058,674 B2 | 8/2018 | Walker et al. | |
| 10,213,334 B2 | 2/2019 | Nofzinger et al. | |
| 10,227,063 B2 | 3/2019 | Abreu | |
| 10,245,176 B2 | 4/2019 | Smith | |
| 2001/0000029 A1 | 3/2001 | Misumi et al. | |
| 2001/0025191 A1 | 9/2001 | Montgomery | |
| 2001/0039442 A1 * | 11/2001 | Gorge | A61F 7/02 607/109 |
| 2001/0045104 A1 | 11/2001 | Bailey, Sr. et al. | |
| 2002/0026226 A1 | 2/2002 | Ein | |
| 2002/0095198 A1 | 7/2002 | Whitebook et al. | |
| 2002/0103520 A1 | 8/2002 | Latham | |
| 2002/0156509 A1 | 10/2002 | Cheung | |
| 2003/0109911 A1 | 6/2003 | Lachenbruch et al. | |
| 2003/0130651 A1 | 7/2003 | Lennox | |
| 2003/0149461 A1 | 8/2003 | Johnson | |
| 2003/0171685 A1 | 9/2003 | Lesser et al. | |
| 2003/0195439 A1 | 10/2003 | Caselnova | |
| 2004/0010178 A1 | 1/2004 | Buckner | |
| 2004/0024432 A1 | 2/2004 | Castilla | |
| 2004/0024438 A1 | 2/2004 | Hoffmann et al. | |
| 2004/0049134 A1 | 3/2004 | Tosaya et al. | |
| 2004/0059400 A1 | 3/2004 | Lin | |
| 2004/0064170 A1 | 4/2004 | Radons et al. | |
| 2004/0073280 A1 | 4/2004 | Dae et al. | |
| 2004/0073281 A1 | 4/2004 | Caselnova | |
| 2004/0159109 A1 | 8/2004 | Harvie | |
| 2004/0171970 A1 | 9/2004 | Schleuniger et al. | |
| 2004/0186541 A1 | 9/2004 | Agarwal et al. | |
| 2004/0193237 A1 * | 9/2004 | Krueger | A61F 7/02 607/96 |
| 2004/0249427 A1 | 12/2004 | Nabilsi | |
| 2005/0065584 A1 | 3/2005 | Schiff et al. | |
| 2005/0087194 A1 | 4/2005 | Scott | |
| 2005/0107851 A1 | 5/2005 | Taboada et al. | |
| 2005/0131504 A1 | 6/2005 | Kim | |
| 2005/0143797 A1 | 6/2005 | Parish et al. | |
| 2006/0024358 A1 | 2/2006 | Santini et al. | |
| 2006/0122673 A1 | 6/2006 | Callister et al. | |
| 2006/0149119 A1 | 7/2006 | Wang | |
| 2006/0161230 A1 | 7/2006 | Craven | |
| 2006/0173396 A1 | 8/2006 | Hatamian et al. | |
| 2006/0198874 A1 | 9/2006 | Stanley | |
| 2006/0235495 A1 | 10/2006 | Tsai | |
| 2006/0235498 A1 | 10/2006 | Mollendorf et al. | |
| 2006/0251743 A1 | 11/2006 | Karita | |
| 2006/0293732 A1 | 12/2006 | Collins et al. | |
| 2007/0010861 A1 | 1/2007 | Anderson et al. | |
| 2007/0055330 A1 | 3/2007 | Rutherford | |
| 2007/0123758 A1 | 5/2007 | Miesel et al. | |
| 2007/0207220 A1 | 9/2007 | Luedtke et al. | |
| 2007/0282249 A1 | 12/2007 | Quisenberry et al. | |
| 2007/0282406 A1 | 12/2007 | Dow | |
| 2008/0015665 A1 | 1/2008 | Lachenbruch | |
| 2008/0033518 A1 | 2/2008 | Rousso et al. | |
| 2008/0046026 A1 | 2/2008 | Pless et al. | |
| 2008/0046047 A1 | 2/2008 | Jacobs | |
| 2008/0097560 A1 | 4/2008 | Radziunas et al. | |
| 2008/0097561 A1 | 4/2008 | Melsky et al. | |
| 2008/0103568 A1 | 5/2008 | Dow | |
| 2008/0140096 A1 | 6/2008 | Svadovskiy | |
| 2008/0168605 A1 | 7/2008 | Wolske | |
| 2008/0188915 A1 | 8/2008 | Mills et al. | |
| 2008/0228248 A1 * | 9/2008 | Guyuron | A61F 7/02 607/108 |
| 2008/0249439 A1 | 10/2008 | Tracey et al. | |
| 2008/0249520 A1 | 10/2008 | Dunning et al. | |
| 2008/0269852 A1 | 10/2008 | Lennox et al. | |
| 2008/0288033 A1 | 11/2008 | Mason et al. | |
| 2008/0300529 A1 | 12/2008 | Reinstein | |
| 2009/0024043 A1 | 1/2009 | MacLeod et al. | |
| 2009/0049694 A1 | 2/2009 | Morris | |
| 2009/0198311 A1 | 8/2009 | Johnson et al. | |
| 2009/0236893 A1 | 9/2009 | Ehlers et al. | |
| 2009/0306748 A1 | 12/2009 | Mollendorf et al. | |
| 2009/0312676 A1 | 12/2009 | Rousso et al. | |
| 2009/0312823 A1 | 12/2009 | Patience et al. | |
| 2010/0030306 A1 * | 2/2010 | Edelman | A61F 7/02 607/104 |
| 2010/0087701 A1 | 4/2010 | Berka et al. | |

(56) References Cited

U.S. PATENT DOCUMENTS

| | | |
|---|---|---|
| 2010/0122398 A1 | 5/2010 | Luciano |
| 2010/0198281 A1 | 8/2010 | Chang et al. |
| 2010/0198318 A1 | 8/2010 | Rogers |
| 2010/0211142 A1 | 8/2010 | Rogers et al. |
| 2010/0241200 A1 | 9/2010 | Bruder et al. |
| 2010/0312317 A1 | 12/2010 | Baltazar |
| 2010/0331752 A1 | 12/2010 | Cumming et al. |
| 2011/0125233 A1 | 5/2011 | Shen et al. |
| 2011/0125238 A1* | 5/2011 | Nofzinger ............ A61F 7/10 607/109 |
| 2011/0184502 A1 | 7/2011 | Bruder |
| 2011/0218421 A1 | 9/2011 | Hempel et al. |
| 2011/0282269 A1 | 11/2011 | Quisenberry et al. |
| 2012/0150268 A1 | 6/2012 | Doherty et al. |
| 2012/0302942 A1 | 11/2012 | DiPierro et al. |
| 2012/0310312 A1 | 12/2012 | Yee |
| 2013/0007945 A1 | 1/2013 | Krondahl |
| 2013/0103125 A1 | 4/2013 | Radspieler et al. |
| 2013/0131464 A1 | 5/2013 | Westbrook et al. |
| 2013/0202668 A1 | 8/2013 | Prost et al. |
| 2013/0289680 A1 | 10/2013 | Hasegawa |
| 2014/0303698 A1 | 10/2014 | Benyaminpour et al. |
| 2014/0343069 A1 | 11/2014 | Laiji et al. |
| 2015/0105687 A1 | 4/2015 | Abreu |
| 2015/0238725 A1 | 8/2015 | Tucker et al. |
| 2016/0361356 A1 | 12/2016 | Roth et al. |
| 2017/0252534 A1 | 9/2017 | Nofzinger |
| 2017/0319815 A1 | 11/2017 | Nofzinger et al. |
| 2017/0333667 A1 | 11/2017 | Tucker |
| 2018/0200476 A1 | 7/2018 | Tucker et al. |
| 2018/0344517 A1 | 12/2018 | Nofzinger |
| 2018/0369536 A1 | 12/2018 | Walker et al. |
| 2019/0133815 A1 | 5/2019 | Nofzinger |

FOREIGN PATENT DOCUMENTS

| | | |
|---|---|---|
| GB | 460200 A | 1/1937 |
| GB | 461294 A | 2/1937 |
| JP | 2-20522 | 2/1990 |
| JP | 10-192331 | 7/1998 |
| JP | H11-001428 A | 1/1999 |
| JP | 11-042282 | 2/1999 |
| JP | 2002536069 A | 10/2002 |
| JP | 2003164496 | 6/2003 |
| JP | 2003260080 A | 9/2003 |
| JP | 2004189999 A | 7/2004 |
| JP | 3730096 B | 10/2005 |
| JP | 2005274013 | 10/2005 |
| JP | 2006102020 | 4/2006 |
| JP | 20007175476 A | 7/2007 |
| WO | WO90/01911 A1 | 3/1990 |
| WO | WO92/20309 A1 | 11/1992 |
| WO | WO94/00086 A1 | 1/1994 |
| WO | WO95/10251 A1 | 4/1995 |
| WO | WO96/10379 A2 | 4/1996 |
| WO | WO96/31136 A1 | 10/1996 |
| WO | WO97/36560 A1 | 10/1997 |
| WO | WO98/56310 A1 | 12/1998 |
| WO | WO99/08632 A1 | 2/1999 |
| WO | WO00/03666 A1 | 1/2000 |
| WO | WO00/09052 A1 | 2/2000 |
| WO | WO01/39704 A1 | 6/2001 |
| WO | WO02/05736 A2 | 1/2002 |
| WO | WO02/34177 A1 | 5/2002 |
| WO | WO03/092539 A2 | 11/2003 |
| WO | WO2004/065862 A2 | 8/2004 |
| WO | WO2004/111741 A1 | 12/2004 |
| WO | WO2005/007060 A2 | 1/2005 |
| WO | WO2005/076806 A2 | 8/2005 |
| WO | WO2005/120428 A1 | 12/2005 |
| WO | WO2006/073915 A2 | 7/2006 |
| WO | WO2006/086086 A2 | 8/2006 |
| WO | WO2007/005026 A1 | 1/2007 |
| WO | WO2007/101039 A1 | 9/2007 |
| WO | WO2008/099017 A1 | 8/2008 |
| WO | WO2008/129357 A2 | 10/2008 |
| WO | WO2008/142650 A1 | 11/2008 |
| WO | WO2008/151260 A2 | 12/2008 |
| WO | WO2009/073208 A1 | 6/2009 |
| WO | WO2009/122336 A1 | 10/2009 |
| WO | WO2009/147413 A1 | 12/2009 |
| WO | WO2011/161571 A1 | 12/2011 |
| WO | WO2012/012683 A1 | 1/2012 |
| WO | WO2012/028730 A1 | 3/2012 |
| WO | WO2012/083151 A1 | 6/2012 |
| WO | WO2015/071810 A1 | 5/2015 |
| WO | WO2015/148411 A1 | 10/2015 |
| WO | WO2016/025323 A1 | 2/2016 |

OTHER PUBLICATIONS

Ahiska et al.; Control of a thermoelectric brain cooler by adaptive neuro-fuzzy interference system; Instrumentation Science and Technology; vol. 36(6); pp. 636-655; Oct. 2008.

Ahmed et al.; Development of a cooling unit for the emergency treatment of head injury; World Congress on Medical Physics and Biomedical Engineering 2006; IFMBE Proceedings; vol. 14(5); Track 19; pp. 3243-3246; Aug. 2006 (copyright 2007).

Alam et al.; Local preoptic / anterior hypothalamic warming alters spontaneous and evoked neuronal activity in the magno-cellular basal forebrain; Brian Research; 696; pp. 221-230; Oct. 1995.

Alam et al.; Preoptic / anterior hypothalamic neurons: thermosensitivity in rapid eye movement sleep; Am. J. Physiol.Regul. Integr. Comp. Physiol.; 269; pp. R1250-R1257; Nov. 1995.

Alfoldi et al.; Brian and core temperatures and peripheral vasomotion during sleep and wakefulness at various ambient temperatures in the rat; Pflugers Arch.; 417; pp. 336-341; Nov. 1990.

Aschoff, Circadian Rhythms in Man, Science, vol. 148, pp. 1427-1432, Jun. 11, 1965.

Baker et al.; Persistence of sleep-temperature coupling after suprachiasmatic nuclei lesions in rats; Am. J. Physiol. Regul. Integr. Comp. Physiol.; 289(3); pp. R827-R838; Sep. 2005.

Bonnet et al.; Heart rate variability: sleep stage, time of night and arousal influences; Electroencephalography and Clinical Neurophysiology; 102(5); pp. 390-396; May 1997.

Boulant et al.; Hypothalamic neuronal responses to peripheral and deep-body temperatures; Am. J. of Physiol.; 225(6); pp. 1371-1374; Dec. 1973.

Boulant et al.; Temperature receptors in the central nervous system; Ann. Rev. Physiol.; 48; pp. 639-654; Mar. 1986.

Boulant et al.; The effects of spinal and skin temperatures on the firing rate and thermosensitivity of preoptic neurones; J. Physiol.; 240(3); pp. 639-660; Aug. 1974.

Boulant; Hypothalamic mechanisms in thermoregulation; Fed. Proc.; 40(14); pp. 2843-2850; Dec. 1981.

Brown; Toe temperature change: a measure of sleep onset?; Walking and Sleeping; 3(4); pp. 353-359; Sep.-Dec. 1979.

Clarkson et al.; Thermal neutral temperature of rats in helium-oxygen, argon-oxygen, and air; Am. J. Physiol.; 222(6); pp. 1494-1498; Jun. 1972.

Crawshaw et al.; Effect of local cooling on sweating rate and cold sensation; Pflugers Arch.; 354(1); pp. 19-27; Mar. 1975.

Diao et al., Cooling and Rewarming for Brain Ischemia or Injury: Theoretical Analysis, Annals of Biomedical Engineering, vol. 31, p. 346-353, Mar. 2003.

Dorr et al.; Effect of Vagus nerve stimulation on serotonergic and noradrenergic transmission; The journal of Pharmacology and experimental therapeutics; 318(2); pp. 890-898; Aug. 2006.

Gong et al.; Sleep-related c-Fos protien expression in the preoptic hypothalamus: effects of ambient warming; Am. J. Physiol. Regul. Integr. Comp. Physiol.; 279(6); pp. R2079-R2088; Dec. 2000.

Gordon; Relationship between preferred ambient temperature and autonomic thermoregulatory function in rat; Am. J. Physiol. Regul. Integr. Comp. Physiol.; 252; pp. R1130-R1137; Jun. 1987.

Gulia et al.; Ambient temperature related sleep changes in rats neonatally treated with capsaicin; Physiol. Behav.; 85(4); pp. 414-418; Jul. 21, 2005.

(56) References Cited

OTHER PUBLICATIONS

Guzman-Marin et al.; Discharge modulation of rat dorsal raphe neurons during sleep and waking: effects of preoptic / basal forebrain warming; Brain Res.; 875(1-2); pp. 23-34; Sep. 1, 2000.

Hajos et al.; The capsaicin sensitivity of the preoptic region is preserved in adult rats pretreated as neonates, but lost in rats pretreated as adults; Naunyn-Schmiedeberg's Arch. Pharmacol.; 324(3); pp. 219-222; Nov. 1983.

Haskell et al.; The effects of high and low ambient temperatures on human sleep stages; Electroencephalogr. Clin. Neurophysiol.; 51(5); pp. 494-501; May 1981.

Hayashi et al., The alerting effects of caffeine, bright light and face washing after a short daytime nap, Clinical Neurophysiology, 114(12), pp. 2268-2278, Dec. 2003.

Hensley et al.; 50 years of computer simulation of the human thermoregulatory system; J. Biomech. Eng.; 135(2); pp. 021005-1-021005-9; Feb. 2013.

Herrington; The heat regulation of small laboratory animals at various environmental temperatures; Am. J. of Physiol.; 129; pp. 123-139; Mar. 31, 1940.

Heuvel et al.; Changes in sleepiness and body temperature precede nocturnal sleep onset: evidence from a polsomnographic study in young men; J. Sleep Res.; 7(3); pp. 159-166; Sep. 1998.

Horne et al., Vehicle accidents related to sleep: a review, Occup Environ Med, vol. 56(5), pp. 289-294 (full text version 13 pgs.), May 1999.

Horne et al.; Exercise and sleep: body-heating effects; Sleep; 6(1); pp. 36-46; Sep. 1983.

Horne et al.; Slow wave sleep elevations after body heating: proximity to sleep and effects of aspirin; Sleep; 10(4); pp. 383-392; Aug. 1987.

Iber et al.; The AASM manual for the scoring of sleep and associtatted events. The rules, terminology and technical specifications; Westchester, IL; © 2007; 57 pages; Oct. 28, 2014; retrieved from the internet (http://www.nswo.nl/userfiles/files/AASM%20-%20Manual%20for%20the%20Scoring%20ofSleep%20and%20Associted%20Events%20-%2005-2007_2.pdf).

Iwata et al., Brain temperature in newborn piglets under selective head cooling with minimal systemic hypothermia, Pediatrics International, 45(2), pp. 163-168; Apr. 2003.

John et al.; Changes in sleep-wakefulness after kainic acid lesion of the preoptic area in rats; Jpn J. Physiol.; 44; pp. 231-242; (year of pub. sufficiently earlier than effective US filing date and any foreign priority date) 1994.

John et al.; Effect of NMDA lesion of the medial preoptic neurons on sleep and other functions; Sleep; 21(6); pp. 587-598; Sep. 15, 1998.

Khubchandani et al.; Functional MRI shows activation of the medial preoptic area during sleep; NeuroImage; 26; pp. 29-35; May 15, 2005.

Krauchi et al.; Circadian rhythm of heat production, heart rate, and skin and core temperature under unmasking conditions in men, American Physiological Society, 267 (3 Pt 2), pp. R819-829, Sep. 1994.

Krauchi et al., Circadian Clues to Sleep Onset Mechanisms, Neuropsychopharmacology, vol. 25, No. S5, pp. S92-96, Nov. 2001.

Krauchi et al.; Functional link between distal vasodilation and sleep-onset latency, Am. J. Physiol. Regulatory Integrative Comp. Physiol., 278(3), pp. R741-748, Mar. 2000.

Krauchi et al., Warm feet promote the rapid onset of sleep, Nature, vol. 401, pp. 36-37, Sep. 2, 1999.

Krilowicz et al.; Regulation of posterior lateral hypothalamic arousal related neuronal discharge by preoptic anterior hypothalamic warming; Brain Res.; 668(1-2); pp. 30-38; Dec. 30, 1994.

Kumar et al.; Ambient temperature that induces maximum sleep in rats; Physiol. Behav.; 98(1-2); pp. 186-191; Aug. 4, 2009.

Kumar et al.; Ambient temperature-dependent thermoregulatory role of REM sleep; Journal of Thermal Biology; 37(5); pp. 392-396; Aug. 2012.

Kumar et al.; Warm sensitive neurons of the preoptic area regulate ambient temperature related changes in sleep in the rat; Indian J. Physiol. Pharmacol.; 55(3); pp. 262-271; Jul.-Sep. 2011.

Kumar; Body temperature and sleep: are they controlled by the same mechanism?; Sleep and Biological Rhythms; 2(2); pp. 103-124; Jun. 2004.

Lack et al.; The rhythms of human sleep propensity and core body temperature; J. Sleep Res.; 5(1); pp. 1-11; Mar. 1996.

Lee et al.; Thermal spot over human body surface (part 1) regional difference in cold spot distribution; J. Human and Living Environment; 2(1); pp. 30-36; (year of pub. sufficiently earlier than effective US filing date and any foreign priority date) 1995.

Leshner et al., Manifestations and Management of Chronic Insomnia in Adults, NIH State-of-the-Science Conference, Final Panel Statement, Bethesda, MD, 36 pgs., Jun. 13-15, 2005.

Libert et al.; Effect of continuous heat exposure on sleep stages in humans; Sleep; 11(2); pp. 195-209; Apr. 1988.

Lu et al.; Effect of lesions of the ventrolateral preoptic nucleus on NREM and REM sleep; J. Neurosci.; 20(10); pp. 3830-3842; May 15, 2000.

Mahapatra et al.; Changes in sleep on chronic exposure to warm and cold ambient temperatures; Physiol. Behav.; 84(2); pp. 287-294; Feb. 15, 2005.

Mallick et al; Basal forebrain thermoregulatory mechanism modulates auto-regulated sleep; Frontiers in Neurology; 10.3389/fneur.2012.00102 (8 pages); Jun. 27, 2012.

McGinity et al.; Hypothalamic regulation of sleep and arousal; Frontiers in Bioscience; 8; pp. s1074-1083; Sep. 1, 2003.

McGinity et al.; Keeping cool: a hypothesis about the mechanisms and functions of slow-wave sleep; TINS; 13(12); pp. 480-487 ; Dec. 1990.

McGinity et al.; Sleep suppression after basal forebrain lesions in the cat; Science; 160(3833); pp. 1253-1255; Jun. 14, 1968.

McKenzie/Mini-Mitter Co.; Mini-Logger® Series 2000, Physiological Data Logging Device; 510K Summary and Premarket Notification (No. K033534); 10 pgs.; Apr. 22, 2004.

Methipara et al.; Preoptic area warming inhibits wake-active neurons in the perifornical lateral hypothalamus; Brain Res.; 960(1-2); pp. 165-173; Jan. 17, 2003.

Morairty et al.; Selective increases in non-rapid eye movement sleep following whole body heating in rats; Brain Res.; 617(1); pp. 10-16; Jul. 16, 1993.

Nadel et al.; Differential thermal sensitivity in the human skin; Pflugers Arch.; 340(1); pp. 71-76; Mar. 1973.

Nakamura; Central circuitries for body temperature regulation and fever; Am. J. Physiol. Regul. Integr. Comp. Phsiol.; 301(5); pp. R1207-R1228; Nov. 2011.

Nakayama et al.; Thermal stimulation of electrical activity of single units of the preoptic region; Am. J. Physiol.; 204(6); pp. 1122-1126; Jun. 1963.

Nakayama; Single unit activity of anterior hypothalamus during local heating; Science; 134(3478); pp. 560-561; Aug. 25, 1961.

Nauta; Hypothalamic regulation of sleep in rats. An experimental study; J. Neurophysiol.; 9; pp. 285-316; Jul. 1946.

Nofzinger et al., Functional Neuroimaging Evidence for Hyperarousal in Insomnia, Am J Psychiatry, 161(11), pp. 2126-2128, Nov. 2004.

Nofzinger et al.; Alterations in regional cerebral glucose metabolism across waking and non-rapid eye movement sleep in depression; Arch. Gen. Psychiatry; 62(4); pp. 387-396; Apr. 2005.

Nofzinger et al.; Frontal cerebral hypothermia: A new approach to the treatment of insomnia; SLEEP; Abstract Suppl.; vol. 32; abstract No. 0881; pp. A287-A288; Jun. 2009.

Nofzinger et al.; Frontal cerebral thermal transfer as a treatment for insomnia: A dose-ranging study; SLEEP; Abstract Suppl.; vol. 34; abstract No. 0534; p. A183; Jun. 2011.

Nofzinger et al.; Regional cerebral metabolic correlates of WASO during NREM sleep in insomnia; J. Clinical Sleep Med.; 2(3); pp. 316-322; Jul. 2006.

Nofzinger/Cereve; SBIR/STTR Grant Submission; Feasibility of frontal cerebral hypothermia as a treatment for insomnia; submitted Dec. 9, 2008.

(56) References Cited

OTHER PUBLICATIONS

Obal et al.; Changes in the brain and core temperatures in relation to the various arousal states in rats in the light and dark periods of the day; Pflugers Arch.; 404(1); pp. 73-79; May 1985.
Olympic Medical; Olympic Cool-Cap System (Product Brochure); 4 pgs.; (year of pub. sufficiently earlier than effective US filing date and any foreign priority date) 2007.
Osborne et al.; Effects of hypothalamic lesions on the body temperature rhythm of the golden hamster; Neuroreport; 6(16); pp. 2187-2192; Nov. 13, 1995.
Parmeggiani et al; Hypothalamic temperature during the sleep cycle at different ambient temperatures; Electroencephalogr. and Clin. Neurophysiol.; 38(6); pp. 589-596; Jun. 1975.
Parmeggiani; Interaction between sleep and thermoregulation: an aspect of the control of behavioral states; Sleep; 10(5); pp. 426-435; Oct. 1987.
Parmeggiani et al.; Sleep and environmental temperature; Arch. Ital. Biol.; 108(2); pp. 369-387; Apr. 1970.
Poole et al.; Body temperature regulation and thermoneutrality in rats; Q. J. Exp. Physiol. Cogn. Med. Sci.; 62(2); pp. 143-149; Apr. 1977.
Raber et al.; Capsaicin 8 % as a cutaneous patch (Qutenza tm): analgesic effect on patients with peripheral neuropathic pain; Acta Neurological Belgica; 115(3); pp. 335-343; Sep. 2015.
Ray et al.; Changes in sleep-wakefulness in the medial preoptic area lesioned rats: role of thermal preference; Behav. Brain Res.; 158(1); pp. 43-52; Mar. 7, 2005.
Ray et al.; Changes in thermal preference, sleep-wakefulness, body temperature and locomotor activity of rats during continuous recording for 24 hours; Behav. Brain Res.; 154(2); pp. 519-526; Oct. 5, 2004.
Raymann et al.; Diminished capability to recognize the optimal temperature for sleep initiation may contribute to poor sleep in elderly people; Sleep; 31(9); pp. 1301-1309; Sep. 2008.
Raymann et al.; Skin deep: enhanced sleep depth by cutaneous temperature manipulation; Brain; 131(PT 2); pp. 500-513; Feb. 2008.
Reyner et al., Evaluation of 'In-Car' Countermeasures to Sleepiness: Cold Air and Radio, Sleep, vol. 21(1), pp. 46-50, Jan. 1998.
Romanovsky et al.; Molecular biology of thermoregulation selected contribution: ambient temperature for experiments in rats: a new method for determining the zone of thermal neutrality; J. Appl. Phsyiol.; 92(6); pp. 2667-2679; Jun. 2002.
Schlaepfer et al.; Vagus nerve stimulation for depression: efficacy and safety in a european study; Psychological medicine; 38; pp. 651-661; May 2008.
Schmidek et al.; Influence of environmental temperature on the sleep-wakefulness cycle in the rat; Physiol. Behav.; 8(2); pp. 363-371; Feb. 1972.
Setokawa et al.; Facilitating effect of cooling the occipital region on nocturnal sleep; Sleep and Biological Rhythms; 5(3); pp. 166-172; Jul. 2007.
Sewitch; Slow wave sleep deficiency insomnia: a problem in thermo-downregulation at sleep onset; Phychophsyiology; 24(2); pp. 200-215; Mar. 1987.
Shapiro et al.; Thermal load alters sleep; Biol. Psychiatry; 26(7); pp. 736-740; Nov. 1989.
Sherin et al.; Activation of ventrolateral preoptic neurons during sleep; Science; 271(5246); pp. 216-219; Jan. 12, 1996.
Srividya et al.; Differences in the effects of medial and lateral preoptic lesions on thermoregulation and sleep in rats; Neuroscience; 139(3); pp. 853-864; Jan. 2006.
Srividya et al.; Sleep changes produced by destruction of medial septal neurons in rats; Neororeport; 15(11); pp. 1831-1835; Aug. 2004.
Sterman e tal.; Forebrain inhibitory mechanisms: sleep patterns induced by basal forebrain stimulation in the behaving cat; Exp. Neurol.; 6; pp. 103-117; Aug. 1962.
Stevens et al.; Regional sensitivity and spatial summation in the warmth sense; Physiol. Behav.; 13(6); pp. 825-836; Dec. 1974.
Stevens et al.; Temperature sensitivity of the body surface over the life span; Somatosens. Mot. Res.; 15(1); pp. 13-28; (year of pub. sufficiently earlier than effective US filing date and any foreign priority date) 1998.
Szymusiak et al.; Ambient temperature-dependence of sleep disturbances produced by basal forebrain damage in rats; Brain Res. Bull.; 12(3); pp. 295-305; Mar. 1984.
Szymusiak et al.; Maximal REM sleep time defines a narrower thermoneutral zone than does minimal metabolic rate; Physiol. Behav.; 26(4); pp. 687-690; Apr. 1981.
Szymusiak et al.; Sleep suppression following kainic acid-induced lesions of the basal forebrain; Exp. Neurol.; 94(3); pp. 598-614; Dec. 1986.
Szymusiak et al.; Sleep-related neuronal discharge in the basal forebrain of cats; Brain Res.; 370(1); pp. 82-92; Apr. 2, 1986.
Tamura et al.; Thermal spot over human body surface (part II) regional difference in warm spot distribution; J. Human and Living Environment; 2(1); pp. 37-42; (year of pub. sufficiently earlier than effective US filing date and any foreign priority date) 1995.
Thannickal et al.; Effect of ambient temperature on brain temperature and sleep-wakefulness in medial preoptic area lesioned rats; Indian J. Pharmacol.; 46(3); pp. 287-297; Jul. 2002.
Van Someren; Mechanisms and functions of coupling between sleep and temperature rhythms; Progress in Brain research; 153; pp. 309-324; Jan. 2006.
Van Someren; More than a maker: interaction between the ciradian regulation of temperature and sleep, age-related changes, and treatment possibilities; Chronobiol. Int.; 17(3); pp. 313-354; May 2000.
Von Economo; Sleep as a problem of localization; The Journal of Nervous and Mental Disease; 71(3); pp. 1-5; Mar. 1930.
Wang et al., Rapid and selective cerebral hypothermia achieved using a cooling helmet, Journal of Neurosurgery, vol. 100 No. 2, pp. 272-277 (full text version 18 pgs), Feb. 2004.
Wikipedia (online encyclopedia); Phase-change Material; 16 pages; retrieved from the internet on Jun. 12, 2015 (https://en.wikipedia.org/wiki/Phase-change_material).
Yavuz et al.; Thermoelectric brain cooler helmet; 6th International Advanced Technologies Symposium (IATS'11); Elazig, Turkey; pp. 120-123; May 16-18, 2011.
Zhang et al.; Chronic vagus nerve stimulation improves autonomic control and attenuates systemic inflammation and heart failure progression in a canine high-rate pacing model; Circulation: Heart Failure; 2(6); pp. 692-699; Nov. 2009.

* cited by examiner

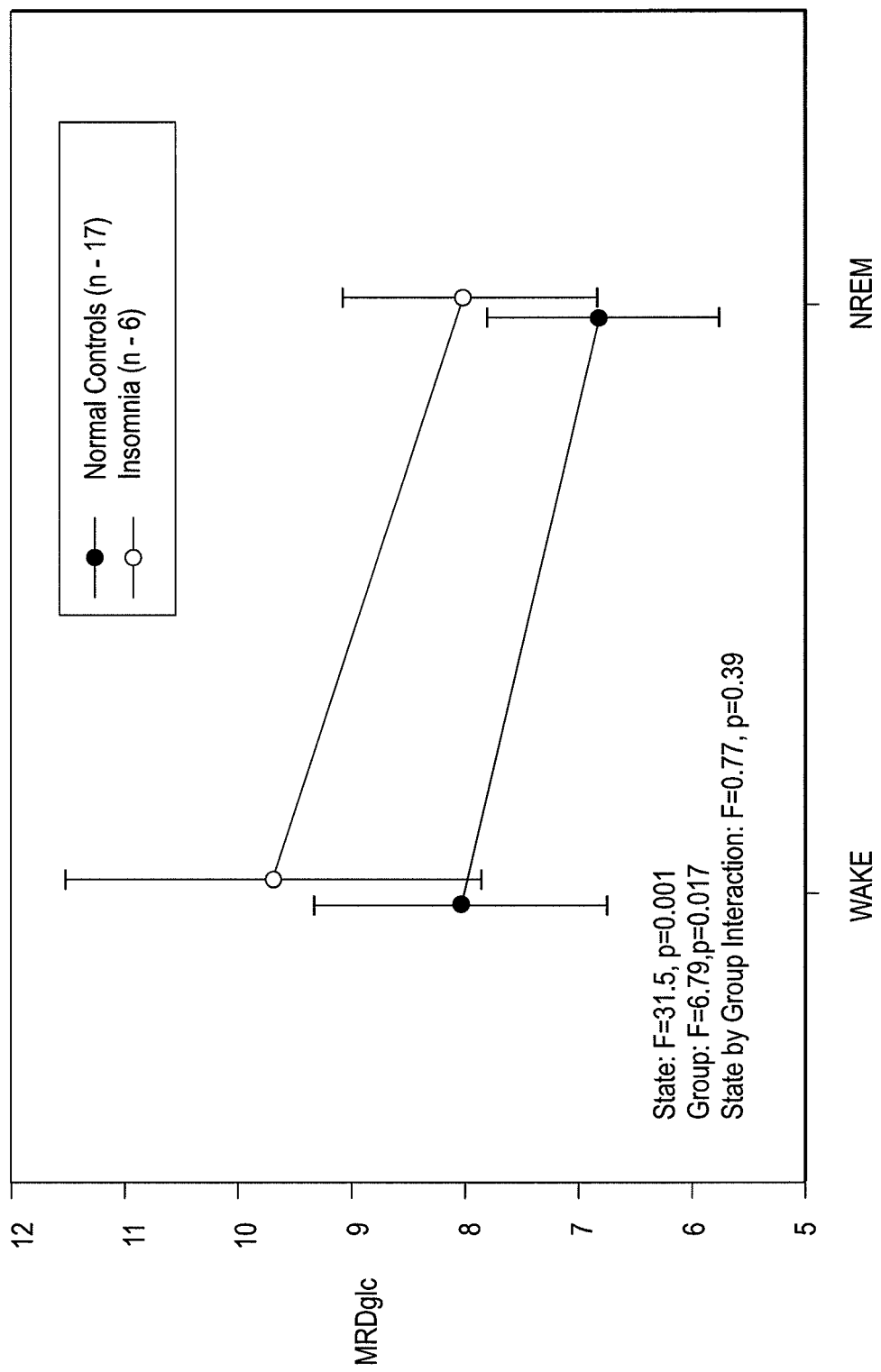

Reductions in waking after
sleep onset (minutes)

Increases in delta
power during sleep

Reductions in relative regional metabolism

NONINVASIVE, REGIONAL BRAIN THERMAL STIMULI FOR THE TREATMENT OF MIGRAINE

CROSS REFERENCE TO RELATED APPLICATIONS

This patent claims priority as a continuation-in-part of U.S. patent application Ser. No. 15/921,528, titled "NON-INVASIVE BRAIN TEMPERATURE REGULATING DEVICES FOR ENHANCING SLEEP," filed on Mar. 14, 2018, which is a continuation-in-part of U.S. patent application Ser. No. 14/435,515, titled "NON-INVASIVE BRAIN TEMPERATURE REGULATING DEVICES FOR ENHANCING SLEEP," filed on Apr. 14, 2015, now U.S. Patent Application Publication No. 2015/0238725, which is a 371 of International Patent Application No. PCT/US2013/070251, filed Nov. 15, 2013, now International Publication No. WO 2014/078630, which claims priority to U.S. Provisional Patent Application No. 61/727,054, filed Nov. 15, 2012, titled "NON-INVASIVE BRAIN COOLING DEVICES FOR ENHANCING SLEEP" and U.S. Provisional Patent Application No. 61/859,161, filed Jul. 26, 2013, titled "APPARATUS AND METHOD FOR MODULATING SLEEP," each of which are herein incorporated by reference in their entirety.

U.S. patent application Ser. No. 15/921,528 also claims priority as a continuation-in-part of U.S. patent application Ser. No. 15/597,057, titled "FOREHEAD COOLING METHOD AND DEVICE TO STIMULATE THE PARASYMPATHETIC NERVOUS SYSTEM FOR THE TREATMENT OF INSOMNIA," filed on May 16, 2017, now U.S. Patent Application Publication No. 2017/0252534, which claims priority as a continuation-in-part of U.S. patent application Ser. No. 14/749,590, filed on Jun. 24, 2015, titled "METHODS, DEVICES AND SYSTEMS FOR TREATING INSOMNIA BY INDUCING FRONTAL CEREBRAL HYPOTHERMIA," now U.S. Pat. No. 9,669,185, which claims priority as a continuation of U.S. patent application Ser. No. 13/868,015, filed Apr. 22, 2013, titled "METHODS, DEVICES AND SYSTEMS FOR TREATING INSOMNIA BY INDUCING FRONTAL CEREBRAL HYPOTHERMIA," now U.S. Pat. No. 9,089,400, which is a continuation of U.S. patent application Ser. No. 13/019,477, filed Feb. 2, 2011, titled "METHODS, DEVICES AND SYSTEMS FOR TREATING INSOMNIA BY INDUCING FRONTAL CEREBRAL HYPOTHERMIA," now U.S. Pat. No. 8,425,583, which claims priority to U.S. Provisional Patent Application No. 61/300,768, filed Feb. 2, 2010 and titled "FRONTAL CEREBRAL HYPOTHERMIA AS A TREATMENT FOR INSOMNIA AND NEUROLOGICAL AND PSYCHIATRIC DISORDERS," each of which are herein incorporated by reference in their entirety.

U.S. patent application Ser. No. 13/019,477 also claims priority as a continuation-in-part of U.S. patent application Ser. No. 11/788,694, filed Apr. 20, 2007, titled "METHOD AND APPARATUS OF NONINVASIVE, REGIONAL BRAIN THERMAL STIMULATION FOR THE TREATMENT OF NEUROLOGICAL DISORDERS," now U.S. Pat. No. 8,236,038, which claims priority to U.S. Provisional Patent Application No. 60/793,680, filed on Apr. 20, 2006, each of which are herein incorporated by reference in their entirety.

U.S. patent application Ser. No. 13/019,477 also claims priority as a continuation-in-part of U.S. patent application Ser. No. 12/288,417, filed Oct. 20, 2008, titled "METHOD AND APPARATUS OF NONINVASIVE, REGIONAL BRAIN THERMAL STIMULATION FOR THE TREATMENT OF NEUROLOGICAL DISORDERS," now U.S. Pat. No. 9,492,313, which is herein incorporated by reference in its entirety.

This application may be related to the following patents and pending applications, each of which is herein incorporated by reference in its entirety: U.S. Pat. No. 8,236,038, filed Ser. No. 11/788,694 (titled "METHOD AND APPARATUS OF NONINVASIVE, REGIONAL BRAIN THERMAL STIMULI FOR THE TREATMENT OF NEUROLOGICAL DISORDERS"); U.S. patent application Ser. No. 13/019,477, filed Feb. 2, 2011 (titled "METHODS, DEVICES AND SYSTEMS FOR TREATING INSOMNIA BY INDUCING FRONTAL CEREBRAL HYPOTHERMIA"); and U.S. patent application Ser. No. 12/288,417, filed Oct. 20, 2008 (titled "METHOD AND APPARATUS OF NONINVASIVE, REGIONAL BRAIN THERMAL STIMULI FOR THE TREATMENT OF NEUROLOGICAL DISORDERS").

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are apparatuses (e.g., device and systems) and methods for treating a patient, including in particular for treating migraines including treating migraines to enhance sleep by non-invasively regulating the temperature of the frontal cortex prior to and/or during sleep.

BACKGROUND

Migraines are a pervasive problem. In particular, migraines may lower overall quality of life, including, but not limited to, quality of sleep. The neurobiology of sleep problems in patients with chronic pain share significant overlaps with those of insomnia suggesting another medical disorder that may benefit from the frontal hypothermia device. Among the most common causes of pain that disrupt sleep is headaches (50% of whom sleep disturbances trigger headaches and 71% of migraine sufferers have migraines that awaken them from sleep).

Sleep is essential for a person's health and wellbeing, yet millions of people do not get enough sleep and many suffer from lack of sleep. Surveys conducted by the U.S. National Science Foundation between 1999 and 2004 found that at least 40 million Americans suffer from over 70 different sleep disorders, and 60 percent of adults report having sleep problems a few nights a week or more. Most of those with these problems go undiagnosed and untreated. In addition, more than 40 percent of adults experience daytime sleepiness severe enough to interfere with their daily activities at least a few days each month, with 20 percent reporting problem sleepiness a few days a week or more. Furthermore, 69 percent of children experience one or more sleep problems a few nights or more during a week.

Insomnia is the most common sleep complaint across all stages of adulthood, and for millions of people, the problem is chronic. Many health and lifestyle factors can contribute to insomnia including stress, depression, medical illnesses, pain, medications, or specific sleeping disorders. There is great need for additional research to better define the nature of chronic insomnia.

Existing treatments of neurological and/or sleeping disorders, including insomnia, include the use of over the counter or prescription drugs and/or behavioral treatments. Prescription drugs are known to aid patients suffering from sleeping disorders, however, these drugs can be quite expensive and potentially addicting. Some medications even become less effective as use continues. Additionally, the prescriptions can have unwanted and harmful side effects.

Other techniques to treat sleeping disorders include a variety of behavioral measures including stimulus control therapy, sleep restriction therapy, relaxation training, cognitive therapy, and sleep hygiene education. While these measures have moderate effectiveness, they are costly, require significant time to implement and require highly trained clinicians to implement.

One treatment technique previously described addresses these issues by using non-invasive and localized or regional thermal stimuli to the brain that helps treat sleep disorders, including insomnia. Specifically, this method may help restore or mimic normal function in the cerebral cortex. The restoration of function in the cerebral cortex plays a significant role in sleep. At the molecular and neuronal levels, hypothesized functions of sleep include the restoration of brain energy metabolism through the replenishment of brain glycogen stores that are depleted during wakefulness and the downscaling of synapses that have been potentiated during waking brain function. A homeostatic sleep drive, or pressure for sleep, is known to build throughout the waking hours and then is discharged during sleep. At the electroencephalographic (EEG) level, this is measured by EEG spectral power in the delta (0.5-4 Hz) frequency band.

These sleep-related processes have some regional specificity for the prefrontal cortex. Slow wave sleep rhythms have both thalamic and cortical components. An anterior dominance of EEG spectral power in the delta EEG spectral power range has been reported. A frontal predominance for the increase in delta power following sleep loss has been also reported. This region of the cortex also plays a prominent role in waking executive functions which are preferentially impaired following sleep deprivation. These sleep deprivation induced cognitive impairments have been related to declines in frontal metabolism after sleep loss. While cerebral metabolism declines globally from waking to NREM sleep, these declines are most pronounced in heteromodal association cortex, including the prefrontal cortex.

Insomnia is associated with global cerebral hypermetabolism. Nofzinger et al. (Am J Psychiatry, 2004) assessed regional cerebral glucose metabolism during both waking and NREM sleep in insomnia patients and healthy subjects using [18F] fluoro-2-deoxy-D-glucose positron emission tomography (PET). Insomnia patients show increased global cerebral glucose metabolism during sleep and wakefulness; and a smaller decline in relative metabolism from wakefulness to sleep in wake-promoting regions of the brain. In a comparison between insomnia and depressed patients, insomnia patients demonstrated increased waking relative metabolism in the prefrontal cortex. Finally, recent research has shown that the amount of wakefulness after sleep onset, or WASO, in insomnia patients correlates with increasing metabolism in the prefrontal cortex during NREM sleep.

The relationship between body temperature and quality of sleep generally has been described in connection with prior research in the field of sleep medicine. Heat loss, via selective vasodilatation of distal skin regions (measured by the distal minus proximal skin temperature gradient (DPG), seems to be a crucial process for the circadian regulation of core body temperature (CBT) and sleepiness (Aschoff 1956; Krauchi and Wirz-Justice 1994, 2002; Krauchi et al. 1998, 2000). Increased DPG before lights off has been noted to promote a rapid onset of sleep, suggesting a link between thermoregulatory and arousal (sleepiness) systems (Krauchi et al. 1999, 2000). Hot environments impair the sleep process including falling asleep and maintaining sleep as well as generating slow wave sleep as the increased ambient temperature interferes with the normal declines in core body temperature associated with the sleep onset process. Finally, rapid and intense temperature drops around the sleep onset or sleeping periods are expected to have an arousing effect (Horne and Reyner 1999; Hayashi et al. 2003). In contrast, the apparatuses and methods described herein minimize such adverse effects from temperature changes through application of a controlled (including relatively constant) thermal regulation over a prolonged period of time to a localized surface of the scalp. Thus, it has been found that noninvasive, regional thermal stimulus to the scalp (e.g., between 10 degrees C. and 40 degrees C.) of the head may help adjust metabolism in the cerebral cortex underlying the stimulus and, thereby, provide treatment for neurological disorders.

Previously described technologies for brain temperature regulation (e.g., cooling) may use a cooling apparatus configured to be placed over the scalp/head immediately atop the frontal cortex region, and cooling of the apparatus is typically applied by circulating coolant, although other cooling mechanisms are discussed. Described herein are advancements and further refinements of this early work, expanding the types of thermal regulation apparatuses that may be used, as well as ways for securing the apparatus to the proper region of a patient's head.

SUMMARY OF THE DISCLOSURE

In general, described herein are non-invasive methods and apparatuses (including devices and systems) for applying thermal therapy to the skin over the prefrontal cortex. In some variations, the apparatuses and methods of using them to treat headaches, including migraines either in an awake or a sleeping subject (or a subject desiring to go to sleep). Treatment may be accomplished by sustained thermal regulation (warming or cooling) in an appropriate therapeutic range and time using one or more phase change materials. Also described are devices and methods to accomplish sustained thermal regulation (cooling) in an appropriate therapeutic range and time. Finally, also descried herein is headgear that is specifically adapted to hold a thermal applicator to provide sustained thermal regulation in the appropriate anatomical region of the head.

For example, described herein are methods, devices and systems for applying hypothermal therapy within highly controlled parameters to the skin over the prefrontal cortex in order to cool the prefrontal cortex and thereby reduce metabolism of this brain region. As described in greater detail below, hypothermic therapy of the prefrontal cortex may ameliorate headache/migraine, including migraine associated sleeping problems such as insomnia. Thus, in many of the therapeutic methods described herein, a device or system includes an applicator having a thermal transfer region (e.g., pad, etc.) that is configured to contact, or be placed in thermal contact, with the patient's skin; specifically the skin over the prefrontal cortex. The applicator may be a mask or garment, and the thermal transfer region may be cooled and temperature controlled by any appropriate means, including fluid cooled (e.g., water cooled) or solid-state (e.g., Peltier device) or some combination thereof.

For example, described herein are methods of treating headaches (e.g., migraines) by non-invasively applying hypothermal therapy to a subject's frontal cortex (including treating migraines/headaches to enhance sleep). The methods may include the steps of: positioning an applicator comprising a thermal transfer region in communication with the subject's skin over the prefrontal cortex; cooling the thermal transfer region to a first temperature consisting of the lowest temperature that may be tolerated by the subject without resulting in discomfort or arousal from sleep; maintaining the first temperature for a first time period extending at least 15 minutes prior to a target good night time; and maintaining a second temperature for a second time period extending at least 15 minutes after the target good night time.

In some variations, the first temperature is between about 10° C. and about 18° C. In some variations, the first temperature (the coolest tolerable temperature) corresponds to the coolest temperature that may be applied by the applicator when worn by the subject and not cause irritation (or arousal); this temperature may be empirically or experimentally determined. For example, the method may include a step of determining the first temperature for the subject.

The step of positioning the applicator may include securing the applicator in position. For example, the applicator may be held in position by straps. In some variations the applicator is adhesively secured. In general, the step of positioning the applicator may include securing the applicator over just the subject's forehead region. In some variations the applicator is limited to the forehead region.

The methods and apparatuses may apply or be used with any subject including human and non-human subject's. These subjects may be referred to herein, equivalently, as patients; a patient may be diagnosed or undiagnosed.

In some variations the step of cooling the thermal transfer region to a first temperature comprises ramping (including gradually ramping) the temperature of the thermal transfer region from ambient temperature to the first temperature over at least five minutes, ten minutes, 15 minutes, etc.

The step of maintaining the first temperature may comprise holding the thermal transfer region at the first temperature for at least 30 minutes, one hour, etc.

In some variations the first temperature is the same temperature as the second temperature (e.g., between 10° C. and 18° C.). However, in some variations the method includes the step of changing the temperature of the thermal transfer region to the second temperature. In general, the second temperature may be a temperature between the first temperature and 30° C. For example, the second temperature may be between about 20° C. and about 25° C. The step of maintaining a second temperature for the second time may comprise maintaining the second temperature for more than one hour, 2 hours, 3 hours, 4 hours, 6 hours, 8 hours, or the entire sleep period. In some variations, the method further comprises adjusting the second temperature based on patient sleep-cycle feedback.

Also described herein are methods of treating migraine (including treating migraines/headaches to enhance sleep) by non-invasively applying hypothermal therapy to a subject's frontal cortex, the method comprising: positioning an applicator comprising a thermal transfer region in communication with the subject's skin over the prefrontal cortex; cooling the thermal transfer region to a first temperature consisting of the lowest temperature that may be tolerated by the subject without resulting in discomfort or arousal from sleep; maintaining the first temperature for at least 15 minutes prior to a target good night time; maintaining the first temperature for at least 30 minutes after the target good night time; and maintaining the temperature at a second temperature between the first temperature and 30° C. for at least 30 minutes.

Also described herein are methods of reducing sleep onset by non-invasively applying hypothermal therapy to a subject's frontal cortex, the method comprising: positioning an applicator comprising a thermal transfer region in communication with the subject's skin over the prefrontal cortex; cooling the thermal transfer region to a first temperature between about 10° C. and about 18° C.; and maintaining the first temperature for a first time period extending at least 15 minutes prior to a target good night time.

Also described herein are methods of sustaining sleep in a subject (e.g., a subject suffering from migraines/headaches) by non-invasively applying hypothermal therapy to the subject's frontal cortex, the method comprising: positioning an applicator comprising a thermal transfer region in communication with the subject's skin over the prefrontal cortex; after a target good night time, maintaining the thermal transfer region at a first temperature consisting of the lowest temperature that may be tolerated by the subject without resulting in discomfort or arousal from sleep; and maintaining the first temperature for a first time period extending at least 30 minutes after the target good night time. For example, the first temperature may be between about 10° C. and about 18° C.

In general the methods of treating insomnia (e.g., by decreasing sleep latency and/or by increasing sustained sleep may be performed by non-invasive cooling, and particularly by cooling the skin over the frontal cortex. In some variations, this cooling is limited to forehead region. The systems and devices described herein generally control the profile of the hypothermal therapy applied so that both the temperature and timing of the dosage is controlled. The system may be configured to apply complex dosing regimens and may be further configured to modify or select the dosing regimen based on feedback from the patient. Feedback may be patient selected (e.g., by adjusting or changing a control input) or may be based of one or more sensors detecting physiological parameters from the patient, such as sleep level, REM/NREM state, or the like.

As described in greater detail below the devices and systems for applying hypothermal therapy as described herein generally include an applicator (e.g., to be secured to or worn by the subject) having a thermal transfer region. The thermal transfer region is cooled. The thermal transfer region is also placed in contact with the skin over the subject's frontal cortex. In general, the applicator and thermal transfer region are configured so that the subject may comfortably and safely wear the device while sleeping or before sleeping (to increase drowsiness). The overall system may be configured to be quiet (so as not to disrupt sleep), and may include one or more controllers for regulating the temperature of the thermal transfer region, as mentioned above. The controller may be a microcontroller (including dedicated hardware, software, firmware, etc.). In some variations the system is configured to be worn by the subject every night, and thus may include a washable, disposable, or replaceable skin-contacting region. For example, the thermal transfer region may be covered by a disposable material or cover that can be replaced nightly with each use. In some variations one or more sensors may also be included to receive patient information and/or performance information on the system; this information may be provided to the controller and may be used to regulate the temperature. Overall, the system may be lightweight and easy to use.

In some of the therapeutic methods described herein, the apparatuses (devices or systems) include and applicator having a thermal transfer region and a phase change material that is configured to contact or be placed in thermal contact, with the patient's skin; specifically the skin over the prefrontal cortex. The thermal transfer region may be further temperature controlled by any appropriate thermal regulator region, include either or both active and passive thermal regulator regions (passive regions may not require active heating/cooling such as by electrically powered devices such as a heater/chiller, Peltier, etc.). For example, a passive thermal regulator may include a phase change material, evaporative cooling, or some combination thereof. Phase changing materials and sustained evaporative cooling may be used specifically to provide appropriate therapeutic cooling in various embodiments a described herein. Any of the applicators and methods described herein (unless the context indicates otherwise) may include an active thermal regulator in addition or in alternative. An active thermal regulator may include a fluid cooled/warmed, a solid state (e.g., Peltier device), or the like.

For example, described herein are methods of treating a migraine by non-invasively applying hypothermal therapy to a subject's frontal cortex, the method comprising: positioning an applicator comprising a thermal transfer region in communication with the subject's skin over the subject's prefrontal cortex; passing cooled fluid through the applicator so that the thermal transfer region is cooled to a first temperature between about 10° C. and about 25° C.; maintaining the first temperature for a first time period extending at least 15 minutes.

The method of treating the migraine may further comprise a method of treating a migraine so that the subject may sleep. Any of these methods may include comprising connecting the applicator to a fluid source, and/or maintaining contact between the subject's skin over the subject's prefrontal cortex and the thermal transfer region so that the metabolism in the prefrontal cortex is slowed.

Positioning the applicator may comprise securing the applicator over just the subject's forehead region. Passing a cooled fluid through the applicator may comprises ramping the temperature of the thermal transfer region from ambient temperature to the first temperature over at least five minutes.

Maintaining the first temperature may comprise maintaining the first temperature for at least 30 minutes. In some variations, maintaining the first temperature comprises maintaining the first temperature for at least one hour.

In general, treating a migraine is a method of reducing sleep onset in the subject. The method of treating the migraine may further comprise a method of preventing the migraine.

For example, a method of treating a migraine by non-invasively applying hypothermal therapy to a subject's frontal cortex so that the subject falls asleep faster may include: coupling an applicator comprising a thermal transfer region to a fluid source; positioning the thermal transfer region in communication with the subject's skin over at least a portion of the subject's frontal cortex, prefrontal cortex or frontal and prefrontal cortex; maintaining the applicator temperature by pumping fluid from the fluid source through the thermal transfer region; and maintaining the temperature for a time period extending at least 15 minutes.

Any of these methods may include maintaining contact between the subject's skin over the subject's frontal cortex, prefrontal cortex or frontal and prefrontal cortex and the thermal transfer region so that the metabolism in the cortex is slowed. Positioning the applicator may comprise securing the applicator in position.

Coupling the applicator may comprise coupling the thermal transfer region to the fluid source via tubing coming out from a middle of a forehead region of the applicator. Positioning the applicator may comprise securing the applicator over just the subject's forehead region.

Maintaining the applicator temperature may comprises maintaining the temperature between about 10° C. and about 25° C. Maintaining the temperature may comprise maintaining the temperature for at least 30 minutes, or maintaining the temperature for at least one hour.

Pumping fluid from the fluid source through the thermal transfer region may comprise altering pumping pressures of the fluid in a rhythmic manner.

A method of treating a migraine by non-invasively applying hypothermal therapy to a subject's frontal cortex so that the subject falls asleep faster may include: coupling an applicator comprising a thermal transfer region to a fluid source, wherein the thermal transfer region comprises one or more channels, through which fluid may be moved; positioning the thermal transfer region in communication with the subject's skin over at least a portion of the subject's frontal cortex, prefrontal cortex or frontal and prefrontal cortex; maintaining the applicator temperature by pumping fluid from the fluid source through the thermal transfer region, wherein the fluid passes into and out of the thermal transfer region via tubing coming out from a middle of a forehead region of the applicator; and maintaining the temperature for a time period extending at least 15 minutes.

BRIEF DESCRIPTION OF THE DRAWINGS

FIG. 1A is a graph illustrating the increase in whole brain metabolism in insomnia during waking and sleep.

DETAILED DESCRIPTION

Figure 1B:
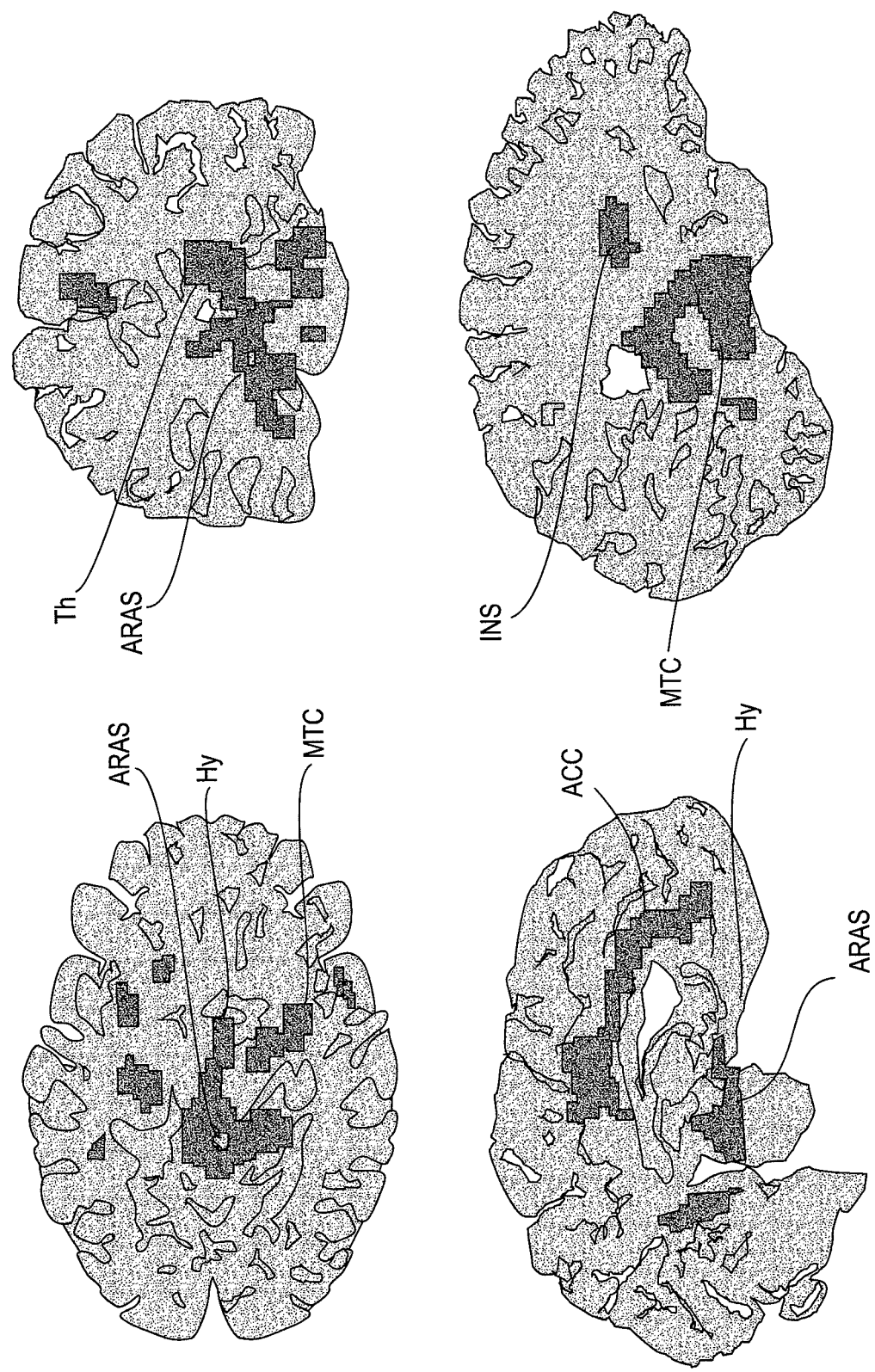
FIG. 1B illustrates brain regions where insomnia patients do not show as great of a decline in relative metabolism from waking to sleep.

In general, described herein are methods and apparatuses (e.g., devices, systems, etc.) for treating a patient suffering from headaches including migraines. This may include, but is not limited to, treating a patient's migraines (or headache) in order to improve sleep. The treatments may be specific to treatment of migraines to improve sleep, including to improve insomnia. Any of the methods of improving sleep (or in some variations improving insomnia) may be include treating the co-morbidity of treating migraines and/or headaches.

As describe above, it has been suggested that the restorative aspects of sleep can be linked regionally with heteromodal association cortex, especially in the frontal regions. The studies described herein clarify the regional cerebral metabolic correlates of this. In the first study, changes in regional cerebral metabolism that occur between waking and sleep in healthy subjects were identified. Fourteen healthy subjects (age range 21 to 49; 10 women and 4 men) underwent concurrent EEG sleep studies and [18F]fluoro-2-deoxy-D-glucose ([18F]-FDG) positron emission tomography (PET) scans during waking and NREM sleep. Whole brain glucose metabolism declined significantly from waking to NREM sleep. Relative decreases in regional metabolism from waking to NREM sleep were found in heteromodal frontal, parietal and temporal cortex, and in dorsomedial and anterior thalamus. These findings are consistent with a restorative role for NREM sleep largely in cortex that subserves essential executive function in waking conscious behavior. In the second study, changes in regional cerebral metabolism were identified that occur between usual NREM sleep and recovery NREM sleep following a night of sleep deprivation. In this study, homeostatic sleep need, or sleep drive, was modulated in a within-subjects design via sleep deprivation. Four young adult healthy male subjects (mean age+s.d.=24.9±1.2 years) received NREM sleep using [18F]fluoro-2-deoxy-D-glucose positron emission tomography ([18F]-FDG PET) assessments after a normal night of sleep and again after 36 hours of sleep deprivation. Both absolute and relative regional cerebral glucose metabolic data were obtained and analyzed. In relation to baseline NREM sleep, subjects' recovery NREM sleep was associated with: (1) increased slow wave activity (an electrophysiological marker of sleep drive); (2) global reductions in whole brain metabolism; and (3) relative reductions in glucose metabolism in broad regions of frontal cortex, with some extension into parietal and temporal cortex. The results demonstrate that the homeostatic recovery function of sleep following sleep deprivation is associated with global reductions in whole brain metabolism as well as greater relative reductions in broad regions of largely frontal, and related parietal and temporal cortex. In other words, sleep deprivation accentuates the decrease in brain metabolism normally seen during NREM sleep. Thus, a medical device that alters metabolism in a pattern similar to that seen in healthy sleep or recovery sleep following sleep deprivation may benefit insomnia patients.

Figure 1C:
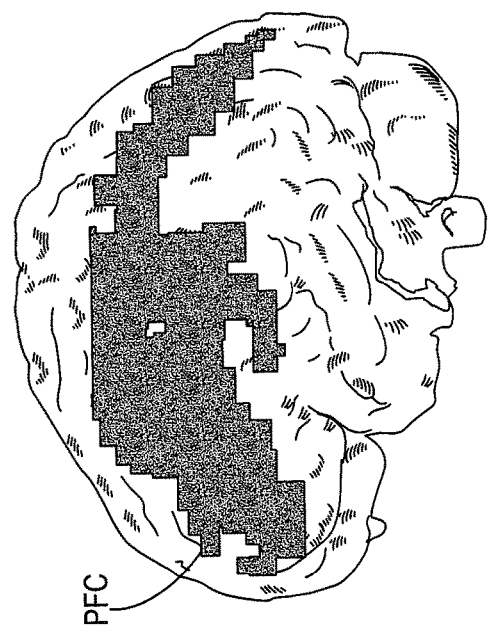
FIG. 1C shows brain regions where relative metabolism is decreased in insomnia patients.
Figure 1C:
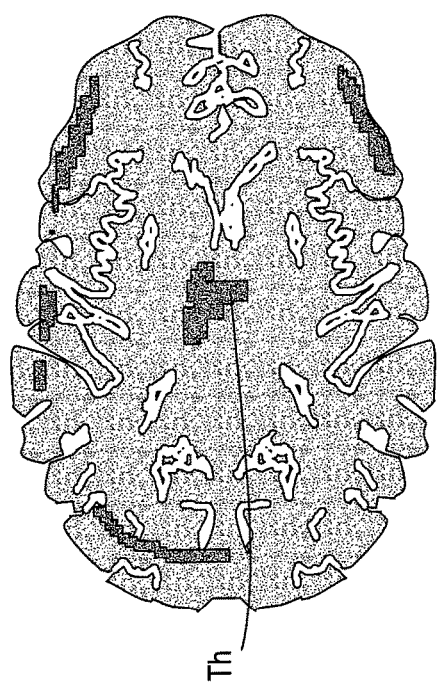
Figure 1C:
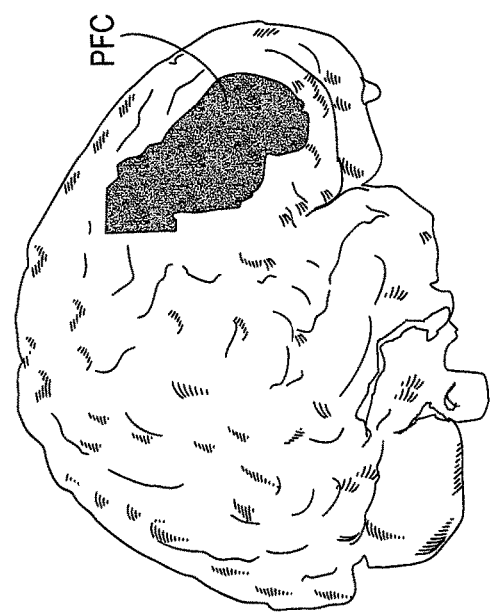
Figure 1C:
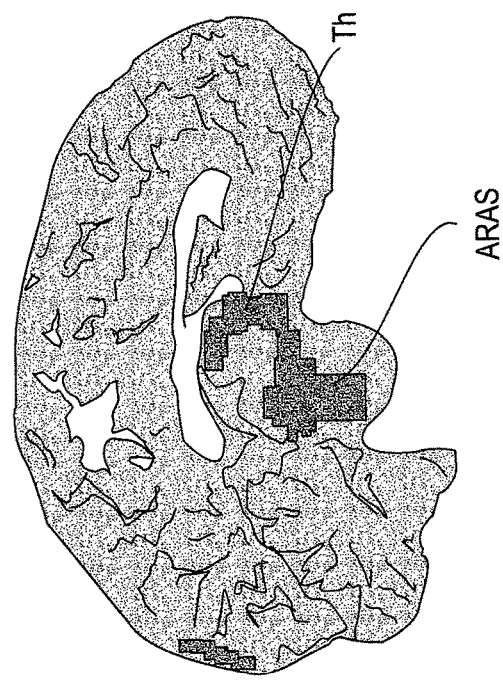

To test this hypothesis, a study of insomnia patients was performed to investigate how these normal changes in brain metabolism become disturbed in insomnia patients. Insomnia patients and healthy subjects completed regional cerebral glucose metabolic assessments during both waking and NREM sleep using [18F]fluoro-2-deoxy-D-glucose positron emission tomography (PET). Insomnia patients showed increased global cerebral glucose metabolism during sleep and wakefulness, as shown in FIG. 1A. A group x state interaction analysis confirmed that insomnia subjects showed a smaller decrease than did healthy subjects in relative metabolism from waking to NREM sleep in the ascending reticular activating system (ARAS), hypothalamus (Hy), thalamus (Th), insular cortex (INS), amygdala and hippocampus (MTC), and in the anterior cingulate (ACC) and medial prefrontal cortices (PFC) (as shown in FIGS. 1B and 1C). While awake, in relation to healthy subjects, insomnia subjects showed relative hypometabolism in a broad region of the frontal cortex bilaterally, left hemispheric superior temporal, parietal and occipital cortices, the thalamus, hypothalamus and brainstem reticular formation. This study demonstrated that subjectively disturbed sleep in insomnia patients is associated with increased brain metabolism. The inability of the insomniac patients to fall asleep may be related to a failure of arousal mechanisms to decline in activity from waking to sleep. Further, their daytime fatigue may reflect decreased activity in prefrontal cortex that results from inefficient sleep. These findings suggest interacting neural networks in the neurobiology of insomnia. These include a general arousal system (ascending reticular formation and hypothalamus), an emotion regulating system (hippocampus, amygdala and anterior cingulate cortex), and a cognitive system (prefrontal cortex). Notably, ascending arousal networks are functionally connected to cortical regions involved in cognitive arousal at the cortical level which can feedback and modulate more primitive brainstem and hypothalamic arousal centers. A medical device that alters metabolism in one or more portions of this network could benefit insomnia patients and produce more restful sleep.

A second study in insomnia patients was conducted to clarify the cerebral metabolic correlates of wakefulness after sleep onset (WASO) in primary insomnia patients testing the hypothesis that insomnia subjects with more WASO would demonstrate increased relative metabolism especially in the prefrontal cortex given the role of this region of the brain in restorative sleep and in cognitive arousal. Fifteen patients who met DSM-IV criteria for primary insomnia completed 1-week sleep diary (subjective) and polysomnographic (objective) assessments of WASO and regional cerebral glucose metabolic assessments during NREM sleep using [18F] fluoro-2-deoxy-D-glucose positron emission tomography (PET). Both subjective and objective WASO positively correlated with NREM sleep-related cerebral glucose metabolism in the pontine tegmentum and in thalamocortical networks in a frontal, anterior temporal, and anterior cingulate distribution. These effects may result from increased activity in arousal systems during sleep and/or to activity in higher order cognitive processes related to goal-directed behavior, conflict monitoring, emotional awareness, anxiety and fear. These processes are thought to be regulated by activity of the prefrontal cortex. A medical device that facilitates the normal reduction in relative metabolism in the prefrontal cortex during sleep could benefit insomnia patients.

As described above, cerebral hypothermia has been utilized in other medical disciplines as a means to reduce metabolic activity in the brain. Theoretical models suggest that application of a cooling stimulus at the scalp surface will cool and subsequently reduce metabolism in the underlying superficial cortex. These observations raised the possibility that a medical device that produced regional cooling to the scalp over the area of the prefrontal cortex, may reduce the hypermetabolism in that region in insomnia patients, allowing them to transition to sleep more easily and to subsequently obtain more restful sleep across the night. It is also conceivable that these cortical effects may have downstream effects on brainstem and hypothalamic centers of sleep/arousal regulation.

Figure 2A:
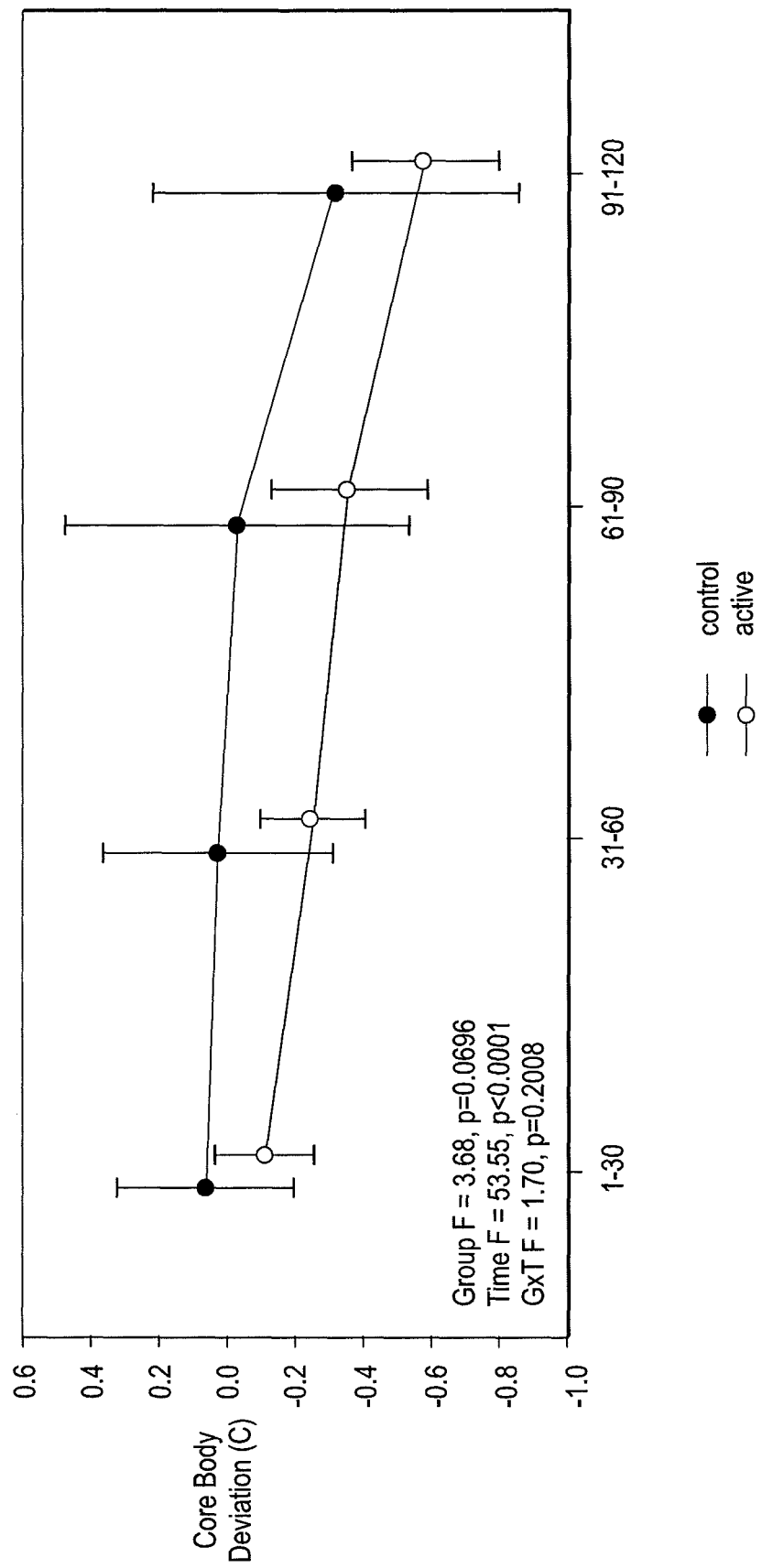
FIG. 2A is a graph illustrating change in the average core body temperature over time in patients treated and untreated using localized frontal hypothermia treatment.
Figure 2B:
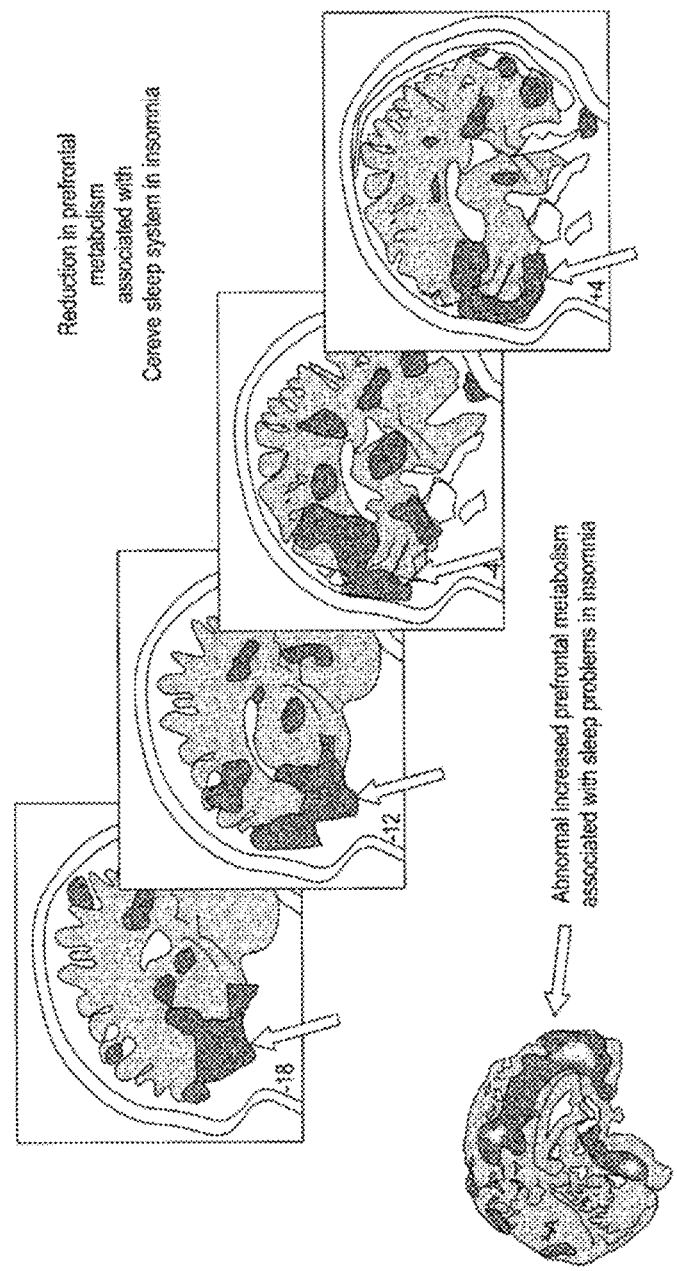
FIG. 2B shows PET scans of an insomniac patient undergoing treatment using frontal hypothermia and illustrating a reversal of prefrontal hypermetabolism.

A device was constructed to test the application of hypothermia applied to the skin over the prefrontal cortex as a method of treating insomnia and sleep-related phenomena. The device itself included a custom sized headpiece to fit the area of the scalp over the frontal cortex that circulated varying temperature fluids and a programmable cooling chamber/pump that provided the cooling and power for circulating the fluid to the headpiece. A study was performed to determine if the device lowered cerebral metabolism in the prefrontal cortex in insomnia patients. The study compared an active treatment (device at 14° C.) vs. a normothermic device comparison (control). Outcome measures included regional cerebral metabolism during sleep as measured by [18F]-FDG PET. 148 subjects were screened, 12 completed sleep studies, and 8 completed all PET imaging studies The data showed that the device reduced cerebral metabolism especially in the prefrontal cortex underneath the device. FIGS. 2A and 2B illustrate some of the findings, and show trends towards reductions in whole brain metabolism, reductions in relative regional metabolism (white arrows showing highlighted regions of FIG. 2B), especially in the prefrontal cortex, an increase in sleepiness and reduction in arousal while the device was worn for 60 minutes prior to bedtime, reductions in minutes of waking, increases in EEG delta spectral power and a reduction in core body temperature around the sleep onset period (FIG. 2A).

FIGS. 3A-3F illustrate some of the additional findings of this work. The study used to achieve these results and the design parameters for this study are described in greater detail below.

Significantly and surprisingly, 9 of 12 (75%) insomnia patients reported positive subjective effects of the device. All subjects encouraged further development of the device based on their experiences and all subjects easily understood/accepted the therapeutic concept for the treatment of their insomnia. They also reported: (1) a clear preference for the device over pills; (2) the device decreased distracting thoughts prior to getting in to bed; (3) the device facilitated sleep maintenance; (4) they experienced a subjective surprise that sleep passed without awareness; and (5) their sleep felt refreshing.

Figure 3C:
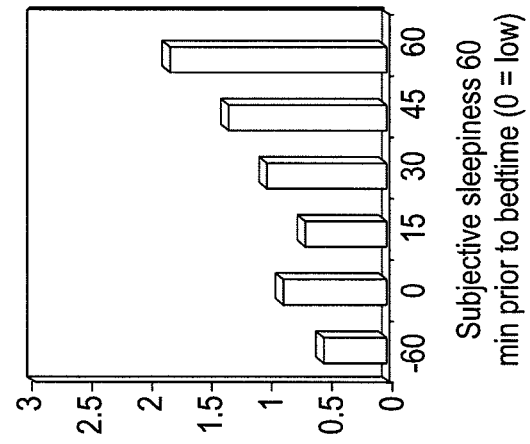
FIG. 3C shows a graph illustrating the increase in subjective sleepiness in insomniac patients treated with prefrontal hypothermia.
Figure 3B:
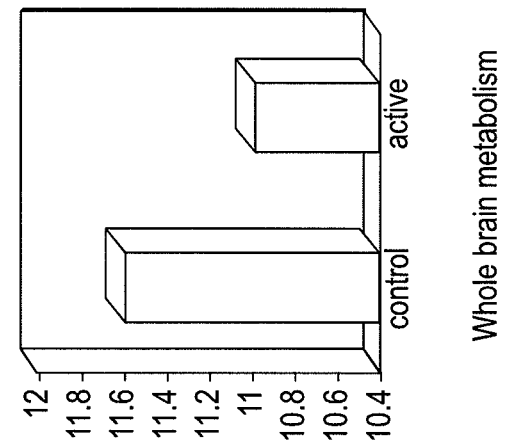
FIG. 3B shows a graph illustrating a decrease in whole brain metabolism (compared to control) in patients treated with prefrontal hypothermia.
Figure 3A:
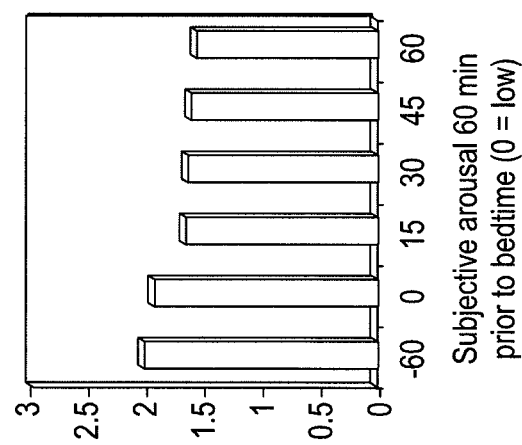
FIG. 3A shows a graph illustrating the decrease in subjective arousal in insomniac patients treated with prefrontal hypothermia as described herein.
Figure 3D:
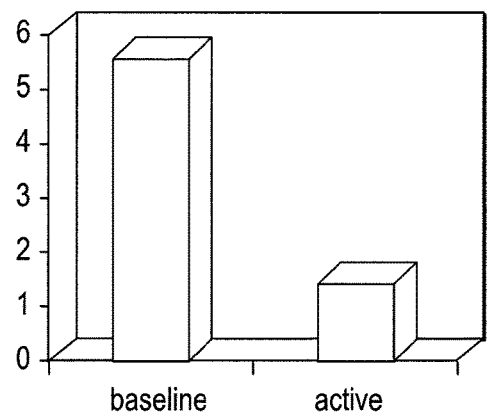
FIG. 3D shows a graph illustrating the decrease a reduction in waking after sleep onset in patients treated with prefrontal hypothermia.
Figure 3E:
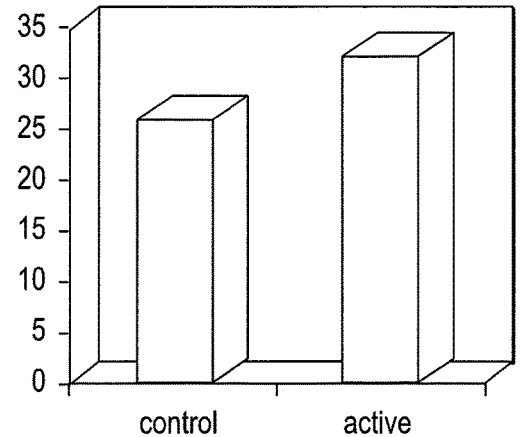
FIG. 3E is a graph illustrating an increase in delta power during sleep in patients treated with prefrontal hypothermia.
Figure 3F:
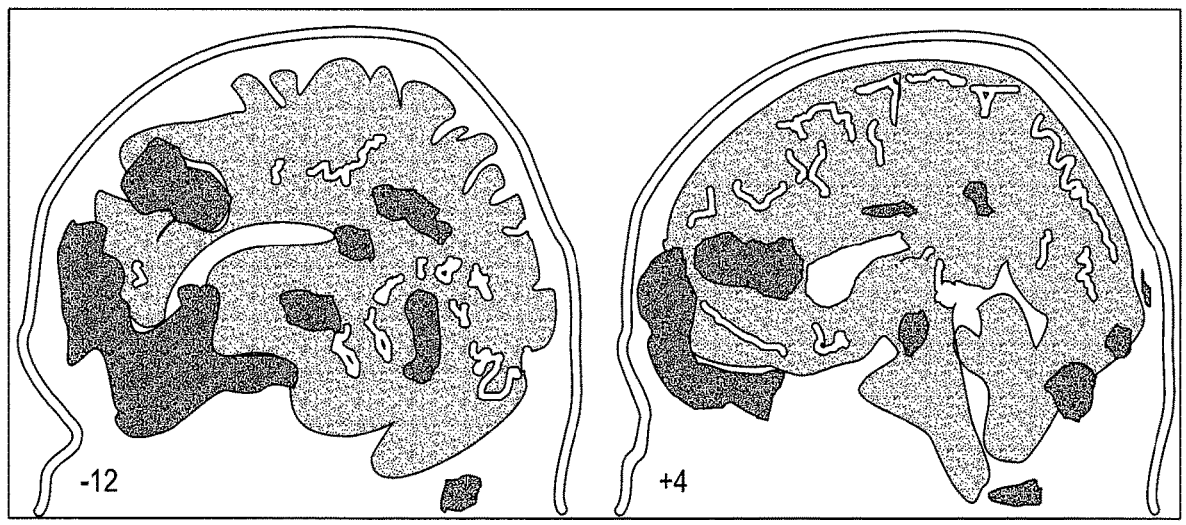
FIG. 3F is a side-by-side comparison of PET scans showing a reduction in regional metabolism in patients treated with prefrontal hypothermia.

As illustrated in FIG. 3A, the subjective arousal of patients treated with frontal/prefrontal hypothermia therapy decreased while wearing the device prior to getting into bed. In FIG. 3A, the x axis represents the 60 minute period prior to the subject getting into bed while wearing the device. The y-axis represents a subjective assessment of arousal (0=no arousal, 3=maximal arousal) measured in 15 minute increments up until the time that the patient got into bed. FIG. 3B shows a graph illustrating a decrease in whole brain metabolism measured by PET scans during NREM sleep between two conditions, an active condition (wearing the device at 14 degrees C. for 60 minutes prior to getting into bed and continuing during sleep until the time of measurement at 20-40 minutes following sleep onset) and a control condition (wearing the device at a thermoneutral 30 degrees C. for 60 minutes prior to getting into bed and continuing during sleep until the time of measurement at 20-40 minutes following sleep onset) in primary insomnia patients. FIG. 3C shows a graph illustrating the increase in subjective sleepiness in insomniac patients treated with prefrontal hypothermia. In FIG. 3C, the x axis represents the 60 minute period prior to the subject getting into bed while wearing the device. The y-axis represents a subjective assessment of sleepiness (0=no sleepiness, 3=maximal sleepiness) measured in 15 minute increments. FIG. 3D shows a graph illustrating the reduction in minutes of waking after sleep onset for the first 40 minutes of sleep during two conditions, an active condition (wearing the device at 14 degrees C. for 60 minutes prior to getting into bed and continuing during sleep for 40 minutes of measurement) and a control condition (wearing the device at a thermoneutral 30 degrees C. for 60 minutes prior to getting into bed and continuing during sleep for 40 minutes of measurement) in primary insomnia patients. FIG. 3E shows a graph illustrating the increase in automated EEG delta power (y-axis) during the first 40 minutes of NREM sleep between two conditions, an active condition (wearing the device at 14 degrees C. for 60 minutes prior to getting into bed and continuing during sleep until the end time of measurement at 40 minutes) and a control condition (wearing the device at a thermoneutral 30 degrees C. for 60 minutes prior to getting into bed and continuing during sleep until the end time of measurement at 40 minutes) in primary insomnia patients. FIG. 3F shows the results of a comparison of regional cerebral metabolism during NREM sleep between two conditions, an active condition (wearing the device at 14 degrees C. for 60 minutes prior to getting into bed and continuing during sleep until the time of PET measurement at 20-40 minutes following sleep onset) and a control condition (wearing the device at a thermoneutral 30 degrees C. for 60 minutes prior to getting into bed and continuing during sleep until the time of PET measurement at 20-40 minutes following sleep onset) in primary insomnia patients. The brain regions highlighted in blue on two different sections through the brain show the areas of the brain, especially in the frontal cortex in the area underneath the device placement, where metabolism was significantly decreased in the active condition vs. the control condition.

Further studies were performed to determine the tolerability and efficacy of a medical device that delivers frontal hypothermia for an extended period (e.g., all night) for the treatment of insomnia. These studies were also performed to further define the specific thermal energy transfer parameters associated with treatment efficacy.

Figure 4A:
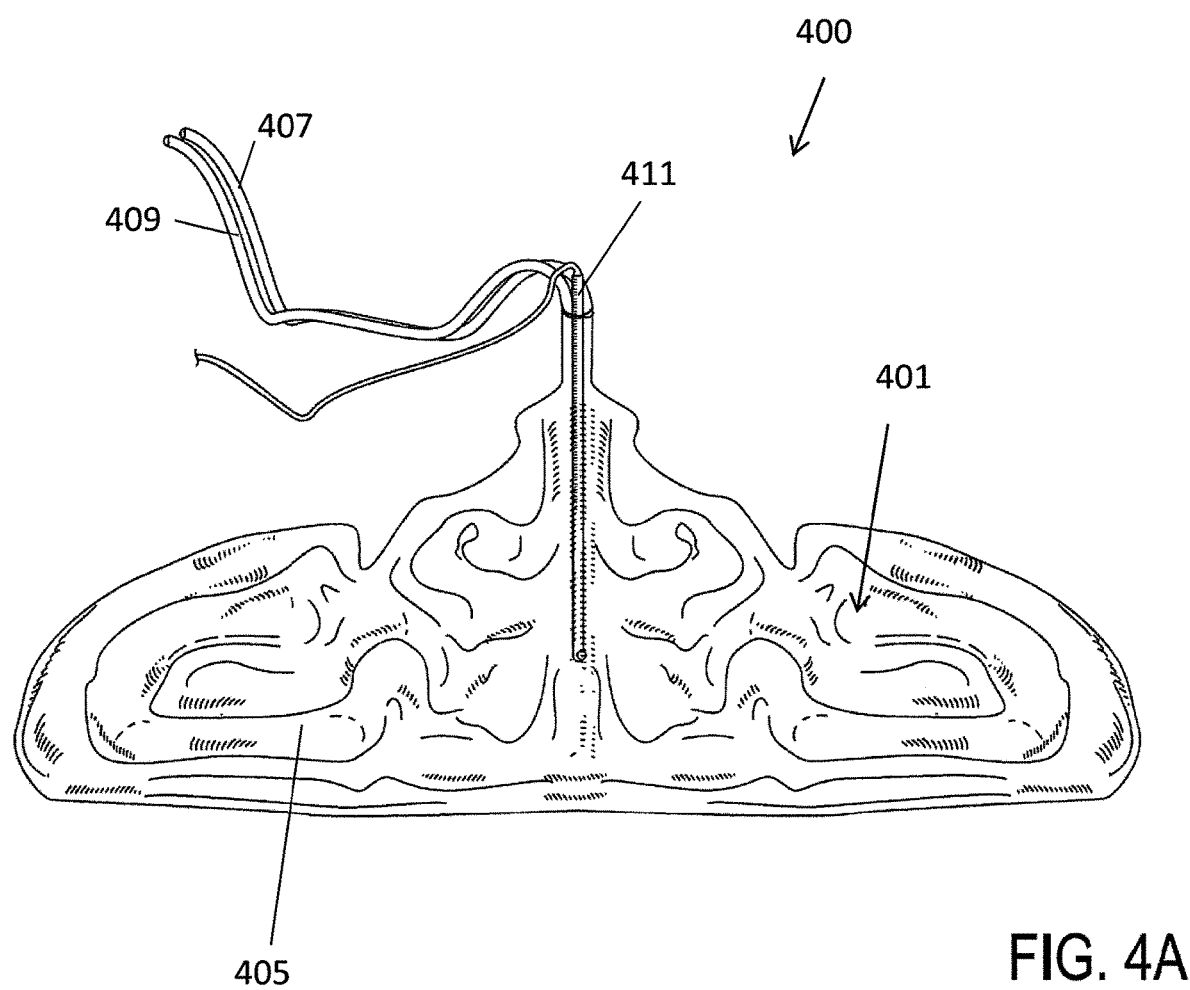
FIG. 4A shows one variation of a headpiece of a device for applying hypothermia.
Figure 4B:
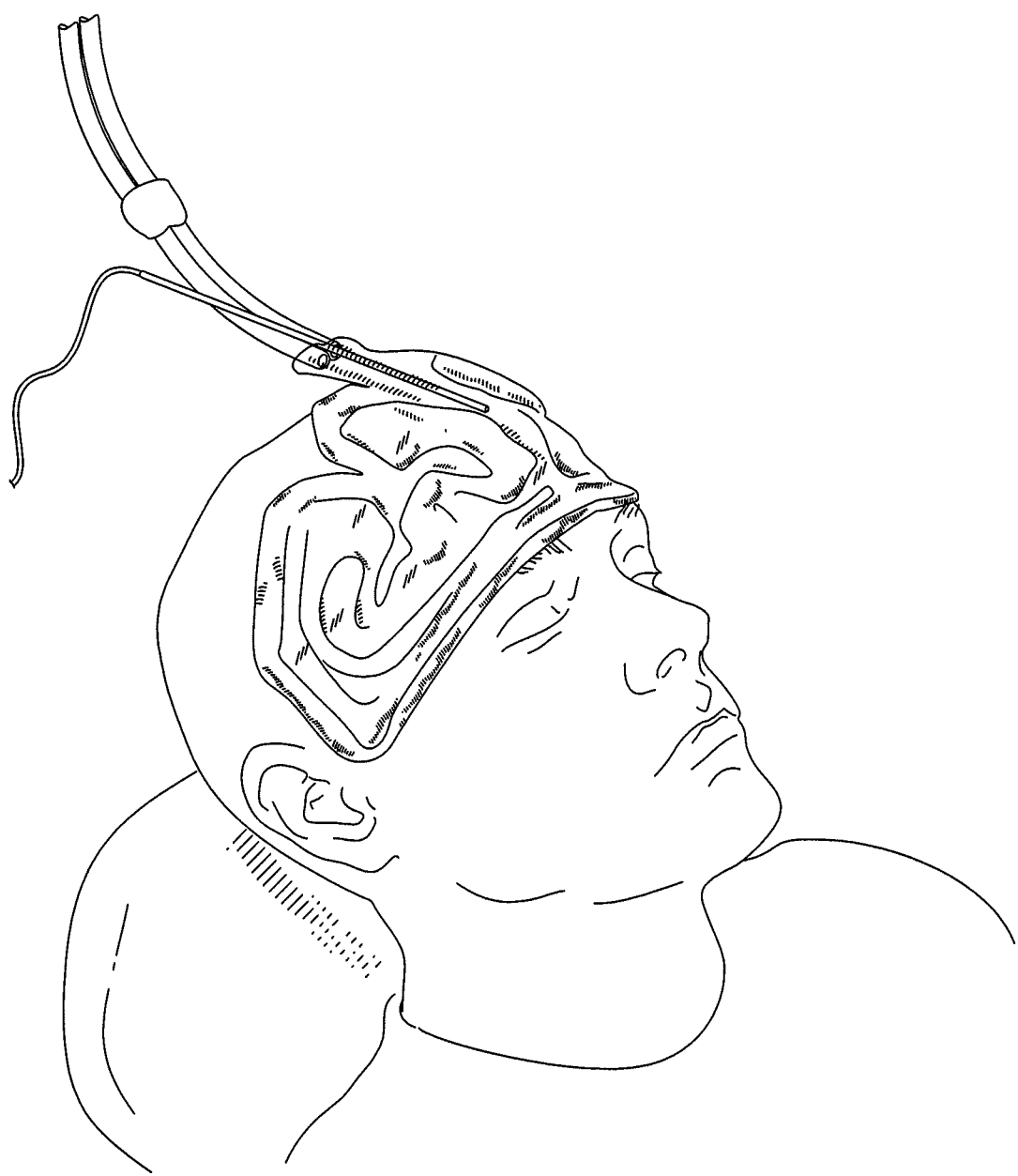
FIG. 4B illustrates the headpiece applied to a subject's head.

Data comparing subjective and objective measures of sleep, and tolerability in mid-life insomnia patients across 4 frontal hypothermia intervention conditions were collected. These included two active and one neutral "doses" of frontal hypothermia device temperature settings and a no device control as follows: (1) a "no device" control; (2) a device at "thermo-neutral" 30° C. and flow rate of 7 gallons per hour; (3) a device at 22° C. and flow rate of 7 gallons per hour; and (4) a device at 14° C. and flow rate of 7 gallons per hour. Based on the flow rates of the active doses, thermal energy will be drawn off of the forehead at a thermal transfer rate ranging from 10-25 W (power). The surface area of the applicator for the experimental device (e.g., the headpiece) is shown in FIGS. 4A and 4B.

Twelve insomnia patients were entered into this study. Each intervention was applied for two nights' duration, separated by at least 2 nights non-intervention sleep at home. The order of presentation of conditions was randomized across subjects in order to control for adaptation and carry over effects from one condition to the next. Primary inclusion criteria included DSM-IV diagnosis of primary insomnia; ages 18-65 (age range minimizes effects of aging on sleep and regional cerebral metabolism that could confound interpretation of studies while encompassing the most prevalent ages for insomnia). Subjects remained alcohol-free and avoided drugs that could affect sleep. Insomnia was defined according to the "General Insomnia Criteria" set forth in the International Classification of Sleep Disorders, 2nd Edition and the criteria for "Insomnia Disorder" in the Research Diagnostic Criteria for Insomnia. These criteria require: (1) a complaint of difficulty falling asleep, staying asleep, awakening too early, or nonrestorative sleep; (2) adequate opportunity for sleep; and (3) evidence for at least one type of daytime impairment related to the sleep complaint. By setting a minimum duration criterion of at least one month and requiring the sleep complaints to be present on most days, we were also consistent with criteria for "Primary Insomnia" in the Diagnostic and Statistical Manual of Mental Disorders, 4th Edition. In order to insure a minimum level of overall severity and comparability with other published data, we required that insomnia participants score >14 on the Insomnia Severity Index. Further, we required that their screening and baseline sleep diaries demonstrate wakefulness after sleep onset of >30 minutes and sleep efficiency <85% on at least 50% of nights, which is consistent with the diagnostic criteria above, and with recommendations for quantitative insomnia criteria.

Primary exclusion criteria included neuropsychiatric disorders that may independently affect sleep, brain function or cognition, such as current major syndromal psychiatric disorders, including DSM-IV mood, anxiety, psychotic, and substance use disorders. Specific exclusionary diagnoses included major depressive disorder, dysthymic disorder, bipolar disorder, panic disorder, obsessive compulsive disorder, generalized anxiety disorder, any psychotic disorder, and any current substance use disorder. Subjects were not excluded for subsyndromal symptoms or disorders in these domains (e.g., minor depression, limited symptom panic attacks). We did not exclude subjects for simple phobia, social phobia, past eating or substance use disorders, specific learning disabilities, or personality disorders. Psychiatric disorders were evaluated using the Structured Clinical Interview for DSM-IV (SCID). Other exclusion criteria include: unstable medical conditions including severe cardiac, liver, kidney, endocrine (e.g. diabetes), hematologic (e.g. porphyria or any bleeding abnormalities), other impairing or unstable medical conditions or impending surgery, central nervous system disorders (e.g., head injury, seizure disorder, multiple sclerosis, tumor), active peptic ulcer disease, inflammatory bowel disease, and arthritis. Individuals with well-controlled health conditions that do not affect sleep or well-being (e.g., well-controlled thyroid disorders, asthma, or ulcer) were not excluded. We excluded women who were pregnant, nursing, or sexually active but not using an effective method of birth control. Subjects who met inclusion criteria and did not have any specific exclusion criteria also had a complete medical history and physical examination, conducted by a physician's assistant, and a set of routine laboratory tests to rule out any unsuspected medical conditions. Specific tests included fasting glucose, complete blood count, liver function tests, serum chemistry, thyroid function tests, urinalysis, and urine drug screen to examine surreptitious sedative use. Other exclusion criteria included: irregular sleep schedules; an AHI (apnea hypopnea index) >20 and oxyhemoglobin desaturations <90% for at least 10% of the night from a diagnostic sleep study; use of medications known to affect sleep or wake function (e.g., hypnotics, benzodiazepines, antidepressants, anxiolytics, antipsychotics, antihistamines, decongestants, beta blockers, corticosteroids); or consumption of more than one alcoholic drink per day, or more than 7 drinks per week.

Subjects were asked to report to the sleep laboratory about 2-3 hours prior to their usual good night time (GNT) for 2 consecutive nights on 4 separate occasions, each separated by at least 2 days. After being studied throughout the night on each night, subjects were allowed to leave the sleep lab after awakening each morning until returning the following evening. On arrival at the sleep lab, subjects were prepared for their studies as follows. Subjects first ingested a temperature monitoring pill (described below) along with their last drinks of fluid. Subjects will remain n.p.o. for the next 3 hours, then allowed water on a p.r.n. basis for the remainder of the study. They were fitted with a belt pack that included a monitoring device to receive the signal from the pill. Subjects were fitted with electrodes and thermistors for monitoring polysomnography, EKG and skin temperature as described below. About 60 minutes prior to good night time (GNT), subjects were seated in a comfortable chair in a sleep lab bedroom. At that time, they filled out questionnaires and rating scales (described below). From the end of completion of questionnaires until 45 minutes prior to GNT (GNT for subjects in the no device condition), technicians ensured that all recording equipment was registering appropriate signals, then at 45 minutes prior to GNT (except for the no device condition), they applied the temperature controlling forehead pad (described below) at a temperature of 30 degrees Celsius (normothermia). After application of the temperature controlling forehead pad, the technician then set the water bath temperature to the desired endpoint for that night's study (14, or 22, or 30 degrees Celsius) where it remained for the remainder of the night of sleep. Equilibration to the desired temperature occurred after 10-15 minutes. Subjects completed rating scales as defined below after the device had been applied, then every 15 minutes until GNT. After completion of the last rating scales at GNT, subjects were asked to get in to bed to sleep undisturbed with monitoring electrodes and thermistors in place for the remainder of the night until their habitual good morning time (GMT). At that time, recording devices and the frontal hypothermia device were removed, morning questionnaires including post-sleep evaluations and subjects were free to leave for the day until returning for the next night's study.

Temperature doses were randomized for the study. The water bath temperatures on the three device interventions included: 14, 22 and 30° Celsius. The flow rate through the mask was 7 gallons per hour at the thermal transfer rate ranging from 10-25 W (power). The lower temperature (about 14° C.) was determined as the limit to which a cold stimulus is experienced by subjects to be cold, yet not uncomfortably cold to the point of producing discomfort. The 30° C. temperature was chosen as a temperature experienced by subjects as "neutral", i.e. not cool or warm, and the 22° C. temperature was chosen as halfway between these two to provide one additional temperature range. To eliminate any order effects of application, the ordering of the three temperature conditions of the frontal hypothermia water bath and the no device condition was randomized across subjects. Preliminary studies show these ranges of temperatures to be well tolerated and without adverse events.

Polysomnography was monitored while frontal hypothermia or no device was applied on each night in the sleep lab. EEG sleep was monitored across the night while subjects slept from GNT to GMT to assess effects of different temperature levels of frontal hypothermia on measures of sleep latency, sleep maintenance and delta EEG spectral power during subsequent sleep. The polysomnographic EEG montage for all these purposes consisted of a single EEG channel (C4/A1-A2), bilateral EOGs referenced to A1-A2, and bipolar submental EMG. Manual and automated scoring of the EEG was performed with emphasis on EEG spectral power in the theta and delta frequency bands as measures of arousal and depth of sleep.

The sleep montage on a sleep disorder screening night conducted prior to any other night of sleep, consisted of a single EEG channel (C4/A1-A2), bilateral EOGs referenced to A1-A2, bipolar submental EMG (electromyogram), single-lead EKG (electrocardiogram), and anterior tibialis EMG. Nasal airflow was monitored by the nasal pressure transducer technique consisting of a standard nasal cannula for $O_2$ delivery, but instead of being attached to an $O_2$ source, it was attached to a pressure transducer to detect pressure swings at the nasal opening. Oral airflow was recorded using a thermistor positioned in front of the mouth. Breathing effort was recorded by respiratory inductance plethysmography (R.I.P.) which employed two elasticized bands, one around the rib cage and one around the abdomen, each containing an embedded wire coil. As the circumference of the two chest wall "compartments" change with breathing effort, the embedded wires are stretched and a signal is generated. $SpO_2$ was non-invasively recorded in the standard fashion by pulse oximetry (Ohmeda, Biox 3700 at fastest possible response time).

Visual sleep stage scoring was also performed. Inter-rater reliability of visual sleep stage scoring was conducted quarterly by the laboratory manager to ensure that technologists maintain consistency over time. Epoch-by-epoch agreement in sleep staging was measured monthly and characterized by Fleiss' modified kappa statistic, intraclass correlations, and absolute % agreement in epochs. Kappa values for REM and wakefulness have values >80, intraclass correlations are >0.85, and % agreement >90%. The following visually scored sleep measures were obtained: sleep latency; time spent asleep; and sleep efficiency.

Sleep latency (SL) is the interval between Good Night Time (GNT) and the first epoch of 10 consecutive minutes of Stage 2-4 NREM or REM sleep, interrupted by no more than one minute of wakefulness. It is expressed in minutes. Time spent asleep (TSA) is the total time spent in any stage of NREM or REM sleep after sleep onset. It is expressed in minutes. Sleep efficiency (SE) is the ratio of time spent asleep to total recording period duration, multiplied by 100. It is expressed as a percentage (SE=[TSA/TRP]×100).

Power spectral analysis was used to quantify the frequency content of the sleep EEG from 0.25-50 Hz. Software was developed in-house to perform spectral analysis of the sleep EEG. Modified periodograms are computed using the Fast Fourier transform (FFT) of non-overlapping 4-second epochs of the sleep EEG. One-minute EEG spectra are obtained as the average of the artifact-free 4-second spectra for a given minute. These 1-minute spectra are time-aligned with the hand scores to allow for the computation of average spectra for various time intervals (e.g., the first NREM period). To further reduce the data for statistical analysis, the spectra can be banded as desired (e.g., a 0.5-4 Hz delta band). This software includes an automated detection routine to eliminate high frequency (predominantly muscle) artifacts (Brunner et al., 1996). Signal processing using power spectral analysis was completed. Power spectral analysis was used quantify EEG power across the frequency range. Power in the delta band was used as dependent measures across studies in the program as a whole. For example, delta power is thought to reflect the homeostatic sleep drive that increases exponentially as a function of prior wakefulness, decreases exponentially during the course of NREM sleep episodes, and is reduced as a function of aging and numerous sleep disorders. Delta power is expressed as micro $V^2$/Hz in the 0.25-4.0 Hz frequency range during NREM sleep.

The temperature applicator (the headpiece) in this example is temperature-regulated by control of the temperature of a circulating fluid ($H_2O$ in this example). The temperature of the internal fluid was monitored and regulated in water bath connected by tubing to the headpiece. The temperature was monitored by the water bath and converted to a signal recorded on the polygraph.

Subject temperature was measured in part by a temperature assessing pill (Vitalsense® system) that was swallowed to record continuous core body temperature over the nights of study in the sleep lab. The pill used a tiny radio transmitter to measure core body temperature and sent the information to a belt pack worn by the subject. The pill passed through the subject undigested and was then discarded with a bowel movement. The device has been approved as safe by the U.S. Food and Drug Administration (FDA) [510(k) number K033534]. Each night, the system was checked for an active signal signifying that the pill had not been passed. If no signal was detected, a new pill was initiated and swallowed. Thermistors were also used to record skin temperature before and during application of frontal hypothermia at: (1) frontal scalp underneath the pad; (2) occipital scalp; and (3) back of non-dominant hand.

Thermistors measured ambient room temperature before and during the application of frontal hypothermia.

As mentioned, in this study the device for applying frontal hypothermia included a temperature-controlling device specifically designed for this application for applying frontal hypothermia. The custom cooling apparatus circulated temperature controlled water, pumped from a water bath to a pad on the patient's forehead. The pad is custom shaped from two laminated sheets of vinyl to cover the target area on the forehead overlaying the prefrontal cortex. The remainder of the head remained uncovered except for a thin nylon spandex cap to retain the pad and hold the tubing. In this exemplary system, a thin layer of hydrogel between the skin and pad improved thermal conductivity and kept the pad against the forehead with minimal air gaps.

The device used in this study included a circulating programmable laboratory water bath (e.g., Polyscience: Polyscience Programmable Model 9112). The system was programmable. The headpiece included a custom shaped vinyl laminate produced with a prescribed flow pattern (e.g., see FIG. 4A) and a boundary matching the surface area of the head targeted for cooling. A hydrogel adhesive may be used to hold the pad snugly against the forehead without applying excessive pressure to the pad. An adhesive may also increase the surface area for contact and provided a high efficiency thermal transfer surface.

In this example, the temperature applicator of the headpiece 400 was used with a retainer device (not shown) to hold the temperature applicator against the subject's head. This head holder in this example was a thin nylon spandex cap that was placed over the laminate to keep it positioned on the head before and during sleep. The applicator 400 includes a thermal transfer region (surface 402) which is configured to be worn against the patient's forehead. As mentioned, an adhesive (e.g., hydrogel, not shown) may be included to help form a thermal contact with the forehead. The applicator 400 shown in FIG. 4 includes channels 405, through which cooled (cooling) thermal transfer fluid may be moved; in this example an inlet 407 and outlet 709 may be included to pump thermal transfer fluid through the applicator. In this example, the applicator also includes at least one sensor 411 comprising a thermistor for monitoring the temperature of the applicator; this information may be fed back to the system for regulating the temperature of the applicator.

The analyses tested differences in sleep between insomniacs and non-insomniacs over a range of active and control temperatures of frontal hypothermia in a within-subjects design presented in a randomized order. The major group difference that was analyzed was the within-subject intervention study comparing the insomnia patients across the various interventions. Multivariate analysis of covariance is an omnibus approach used to compare multiple measures between groups while controlling for known covariates such as age and gender. A repeated domain was added to the model to explore differences in measures across interventions. The results tested whether there is a linear effect from baseline to neutral temperature to 22° C. to 14° C. temperature of the circulating water at identical flow rates and using identical thermal transfer pad over the forehead. Age- and gender-matched historical control subjects' data are shown on the graphical results displayed in FIGS. 5A-5L to illustrate relationships to normative sleep.

For the 12 primary insomnia subjects examined (9 women/3 men, with a mean age+s.d. of 44.62+12.5 years) compared to 12 healthy age- and gender-matched historical control subjects, the results show a remarkable effect on hypothermic treatment, particularly at lower temperatures (closer to the 14° C. parameter). The graphs shown in FIGS. 5A-5L also provide a comparison in relation to normative measures for healthy control subjects studied in the same laboratory environment.

These results show that that the thermal effect (the hypothermic effect) applied non-invasively to the subject's skin adjacent to the prefrontal cortex has a temperature-dependent effect. This effect may also be time-dependent, in applying the therapy for a time before the GNT and for some period after GNT, including the entire night or a portion of the night during sleep. The effects and parameters are illustrated below.

Figure 5A:
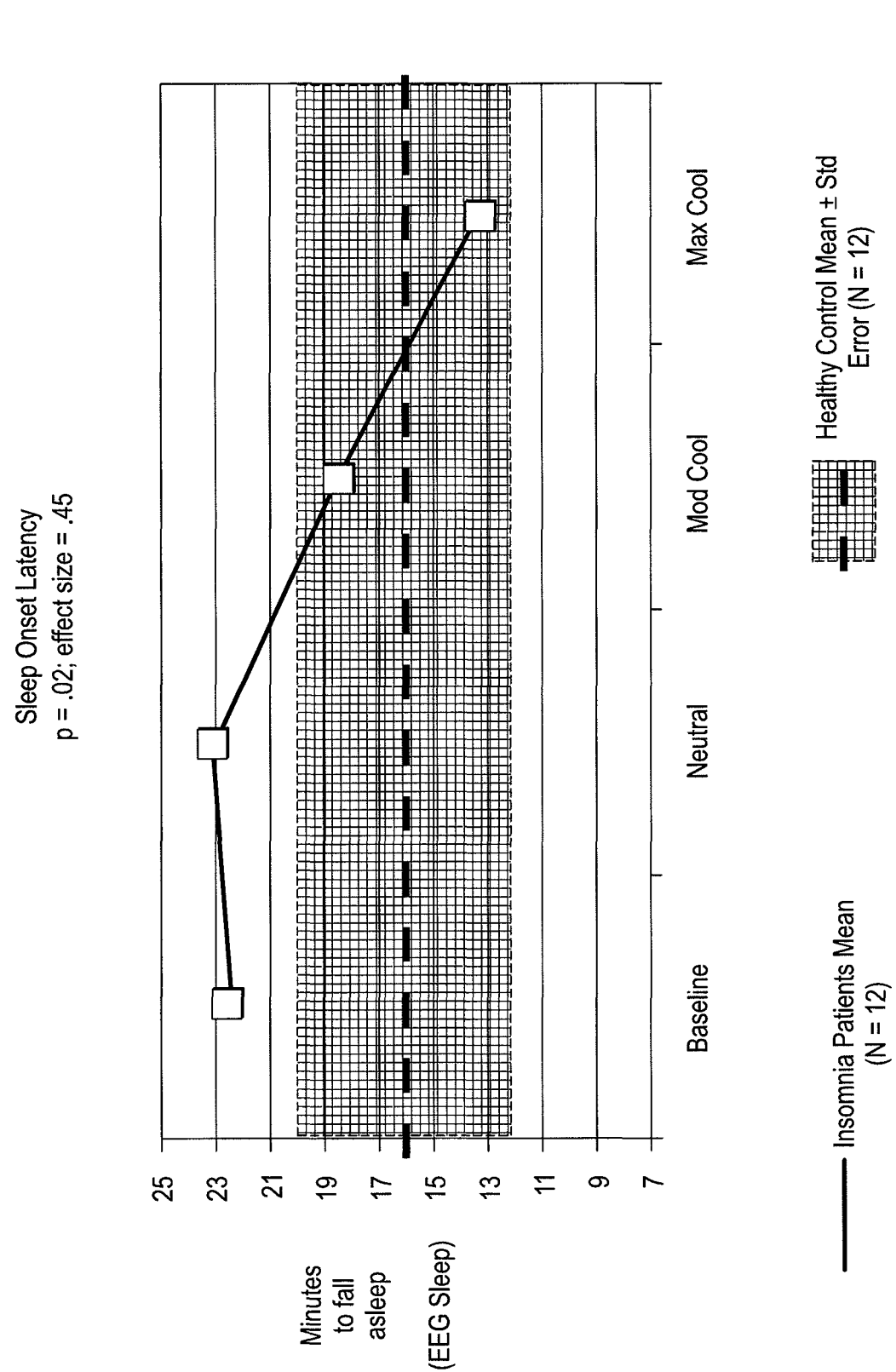
FIG. 5A shows the effect of one variation of a device for applying prefrontal hypothermia on sleep onset latency in an insomniac patient compared to non-insomniac.
Figure 5B:
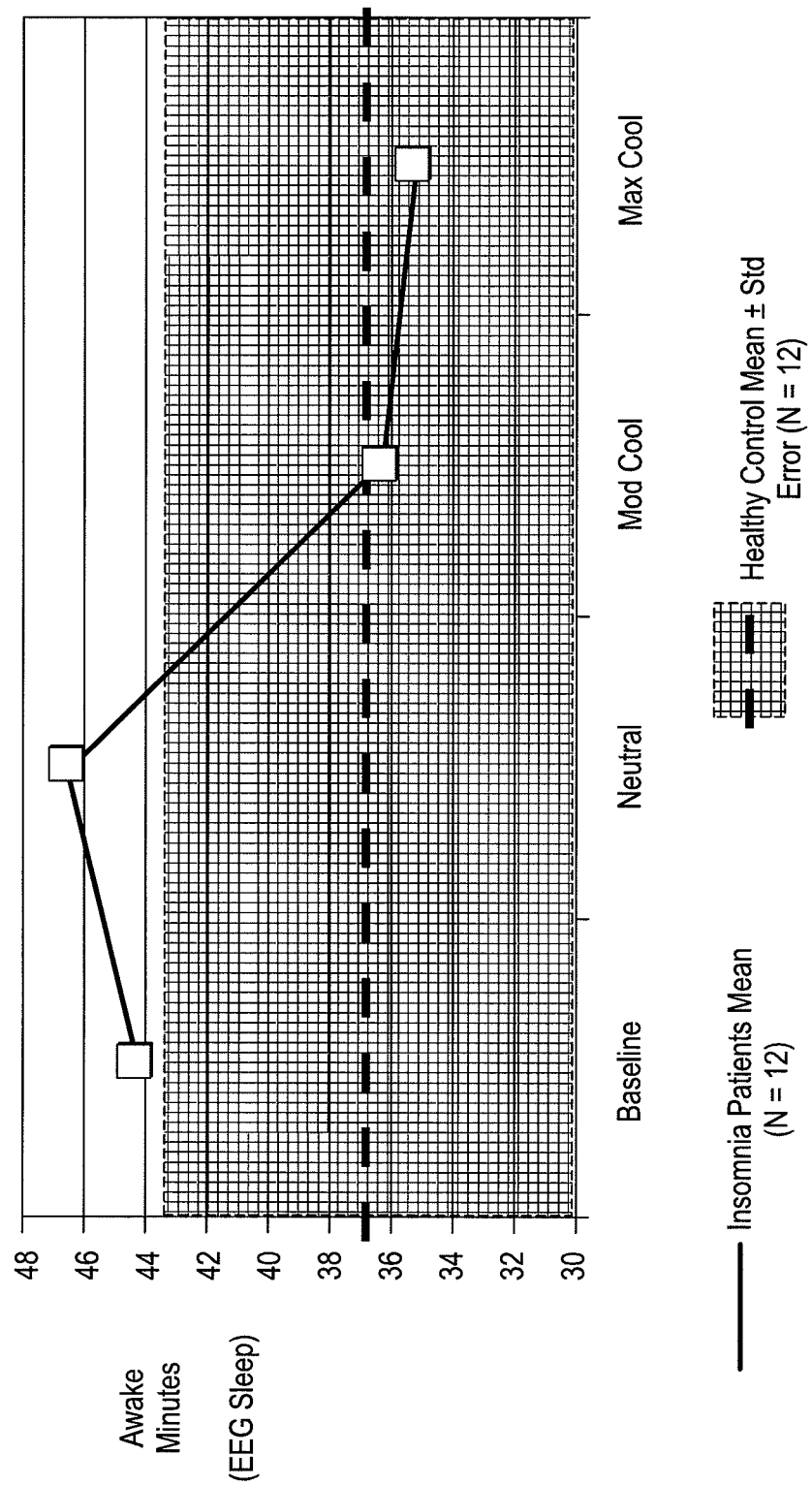
FIG. 5B shows the effect of one variation of a device for applying prefrontal hypothermia on awake after sleep onset in an insomniac patient compared to non-insomniac.

For example, the system typically applies (non-invasively) hypothermic therapy to a patient's skin above (adjacent) to the prefrontal cortex for an extended period of time at a temperature that is not perceived as uncomfortably cold (e.g., typically greater than or about 10° C., such as 14° C.). This therapy typically shortens the time to fall asleep, as illustrated in FIG. 5A. In FIG. 5A the sleep onset latency of insomniac patients experiencing cooling (both moderate cooling at 22° C. and maximum cooling at 14° C.) was significantly shorter than in untreated subjects. This effect was also seen to be temperature dependent; greater cooling ("max cool") at 14° C. had a more rapid sleep onset.

Figure 5C:
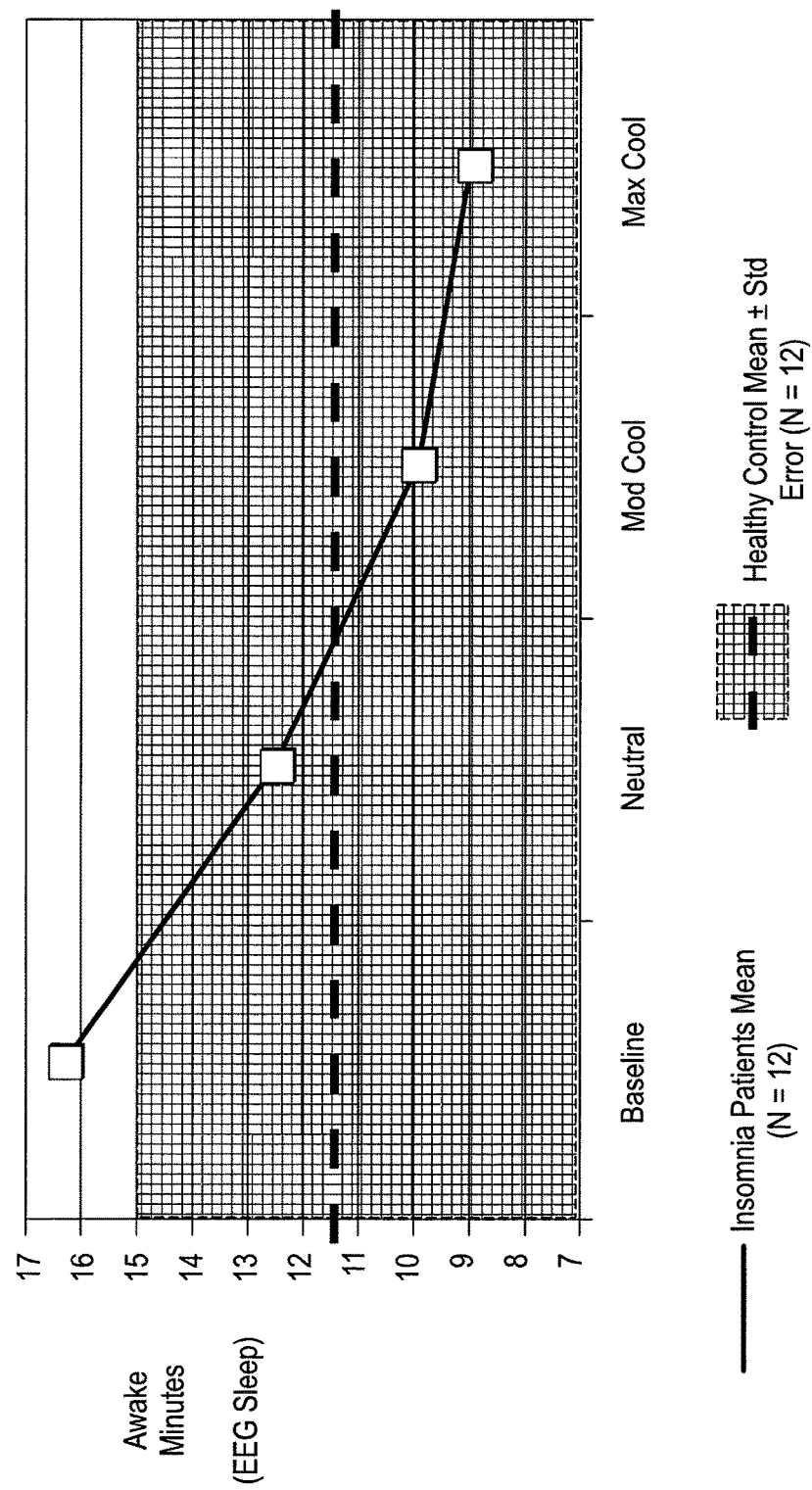
FIG. 5C shows the effect of one variation of a device for applying prefrontal hypothermia on wakefulness in the first half of the night in an insomniac patient compared to non-insomniac.
Figure 5D:
FIG. 5D shows the effect of one variation of a device for applying prefrontal hypothermia on wakefulness in the second half of the night in an insomniac patient compared to non-insomniac.

In addition to helping the insomniac patient fall asleep more quickly, the system also enhanced and increased the duration of sleep, as shown in FIGS. 5B-5E, an effect which was also temperature dependent. For example, hypothermic treatment also diminished wakefulness after sleep onset; in FIGS. 5B, 5C and 5D, the time the insomniac patient was awake after onset of sleep fell to within normal controls, particularly in the first half of the night, as shown in FIG. 5C. Although this preliminary work is not definitive with respect to the effect in the first half of the night compared to the second half, it suggests that it may be sufficiently effective to provide hypothermic treatment for at least the first half of the night (e.g., anticipated sleep period). For example, for between about 2-6 hours, and less effective beyond that point. Alternatively, it may be beneficial to shift the temperature applied either up or down, later during sleep in order to further regulate the patient's sleep.

Figure 5E:
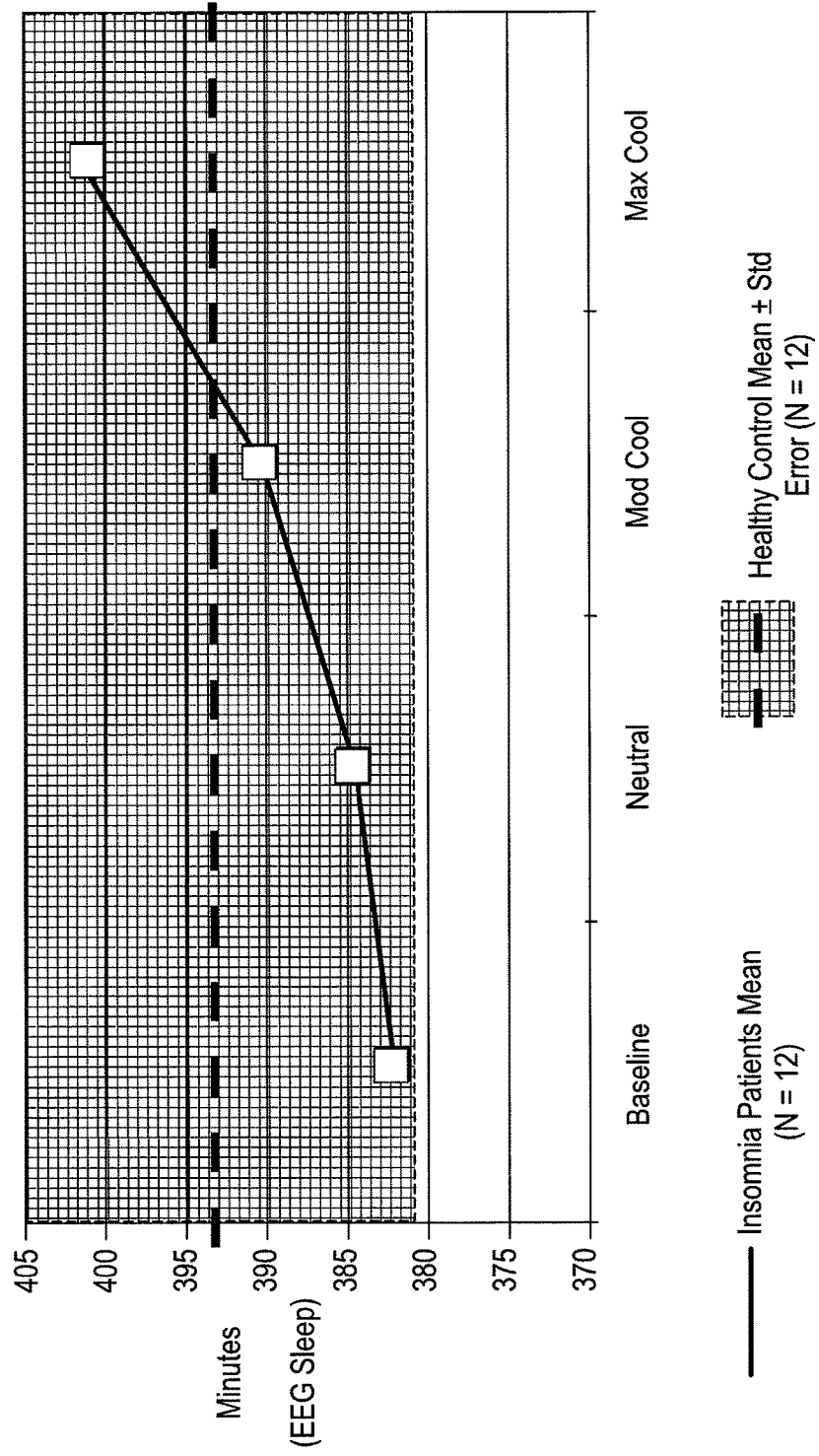
FIG. 5E shows the effect of one variation of a device for applying prefrontal hypothermia on total sleep time in an insomniac patient compared to non-insomniac.
Figure 5F:
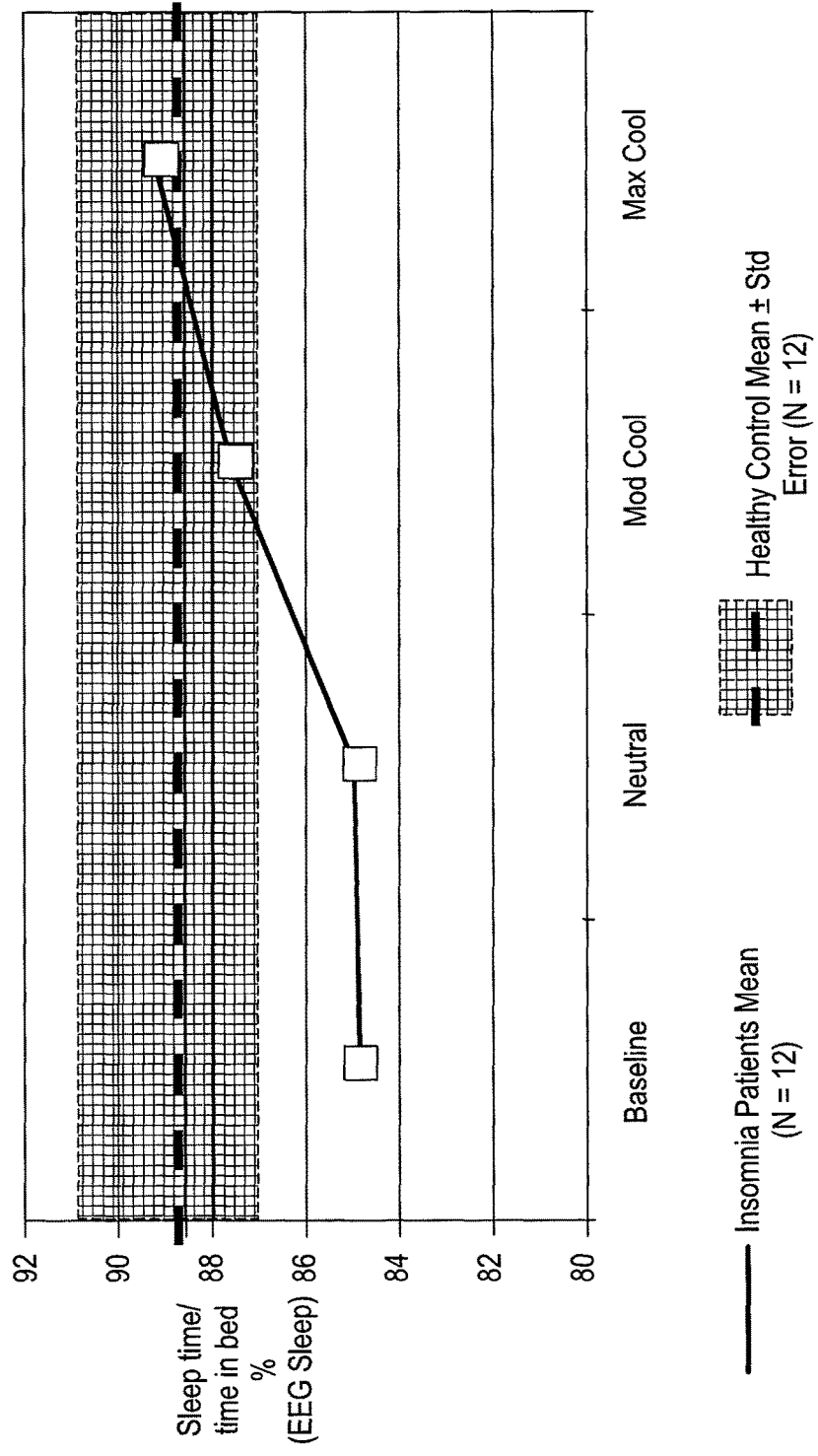
FIG. 5F shows the effect of one variation of a device for applying prefrontal hypothermia on sleep efficiency in an insomniac patient compared to non-insomniac.
Figure 5G:
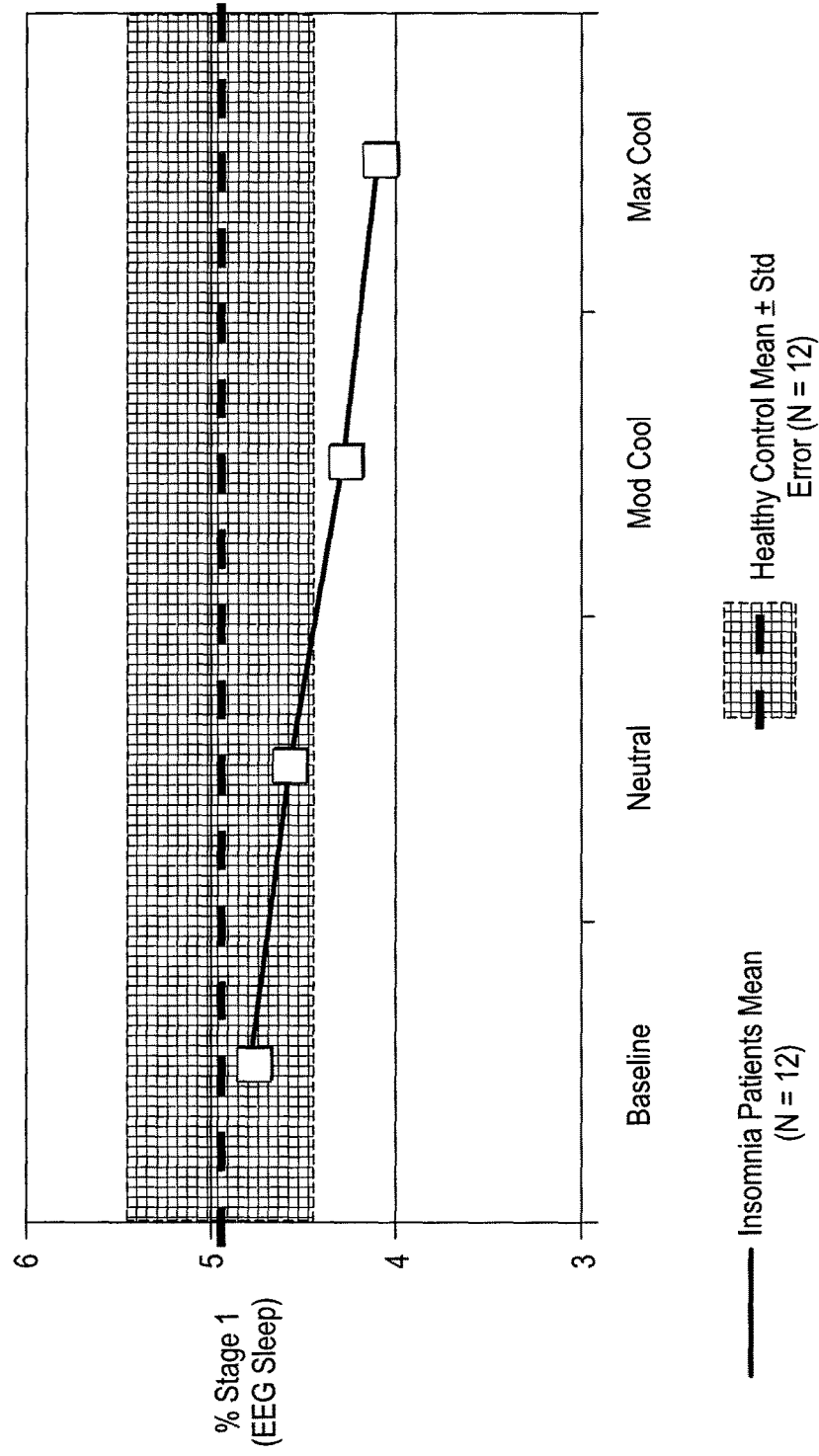
FIG. 5G shows the effect of one variation of a device for applying prefrontal hypothermia on the percentage of stage 1 sleep in an insomniac patient compared to non-insomniac.
Figure 5H:
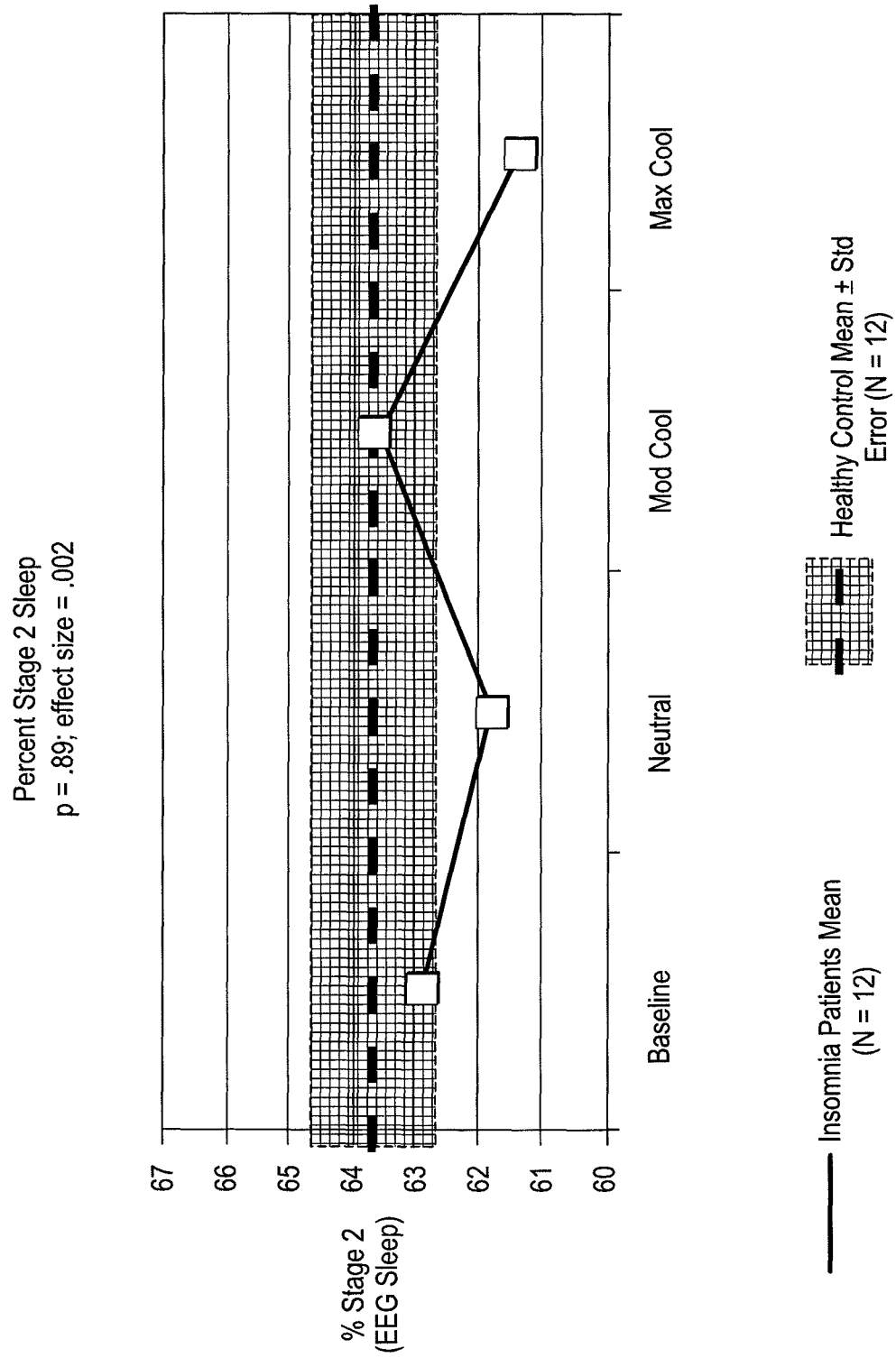
FIG. 5H shows the effect of one variation of a device for applying prefrontal hypothermia on the percentage of stage 2 sleep in an insomniac patient compared to non-insomniac.
Figure 5I:
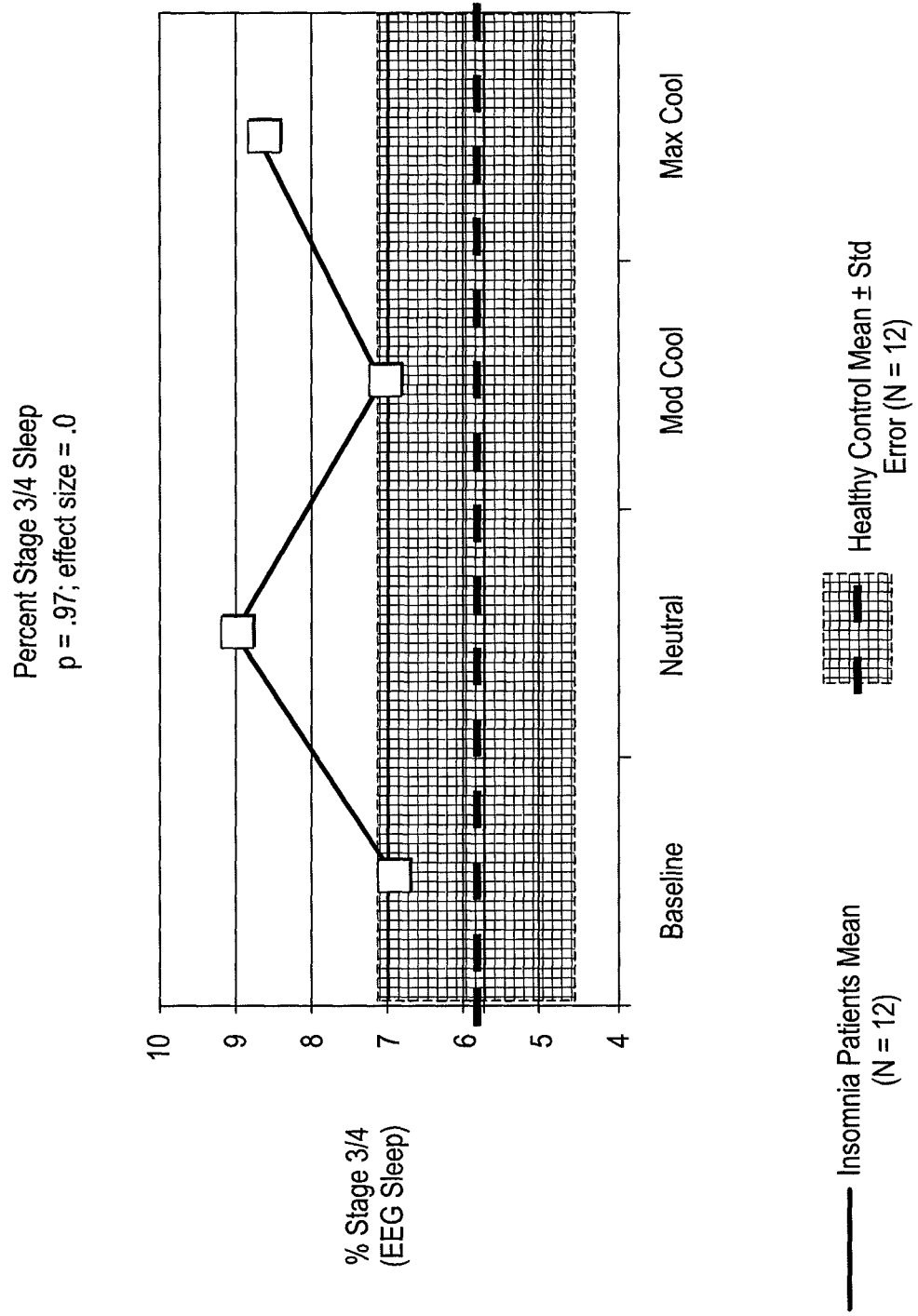
FIG. 5I shows the effect of one variation of a device for applying prefrontal hypothermia on the percentage of stages 3/4 sleep in an insomniac patient compared to non-insomniac.
Figure 5J:
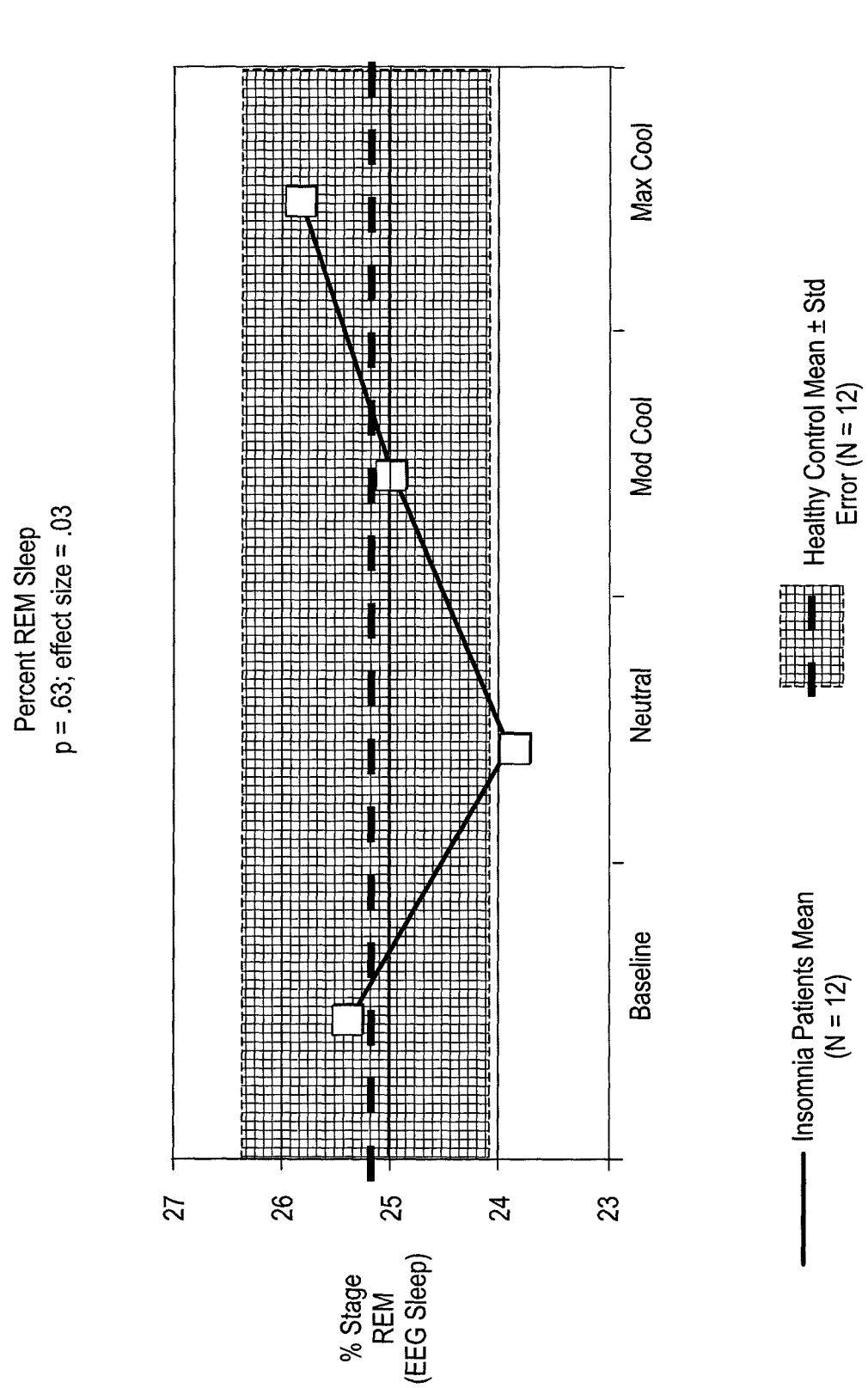
FIG. 5J shows the effect of one variation of a device for applying prefrontal hypothermia on the percentage of REM sleep in an insomniac patient compared to non-insomniac.
Figure 5K:
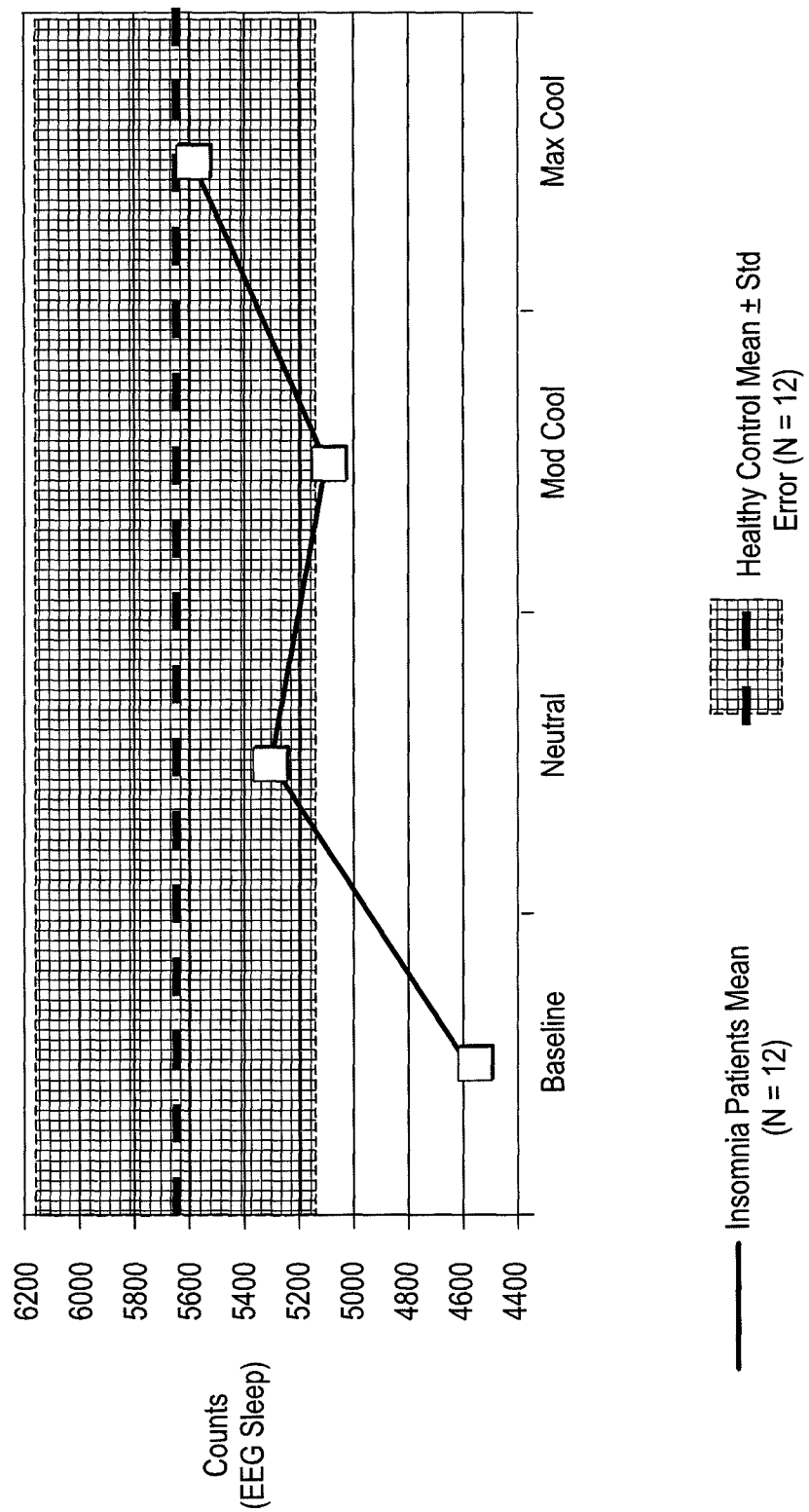
FIG. 5K shows the effect of one variation of a device for applying prefrontal hypothermia on the number of whole night delta counts in an insomniac patient compared to non-insomniac.
Figure 5L:
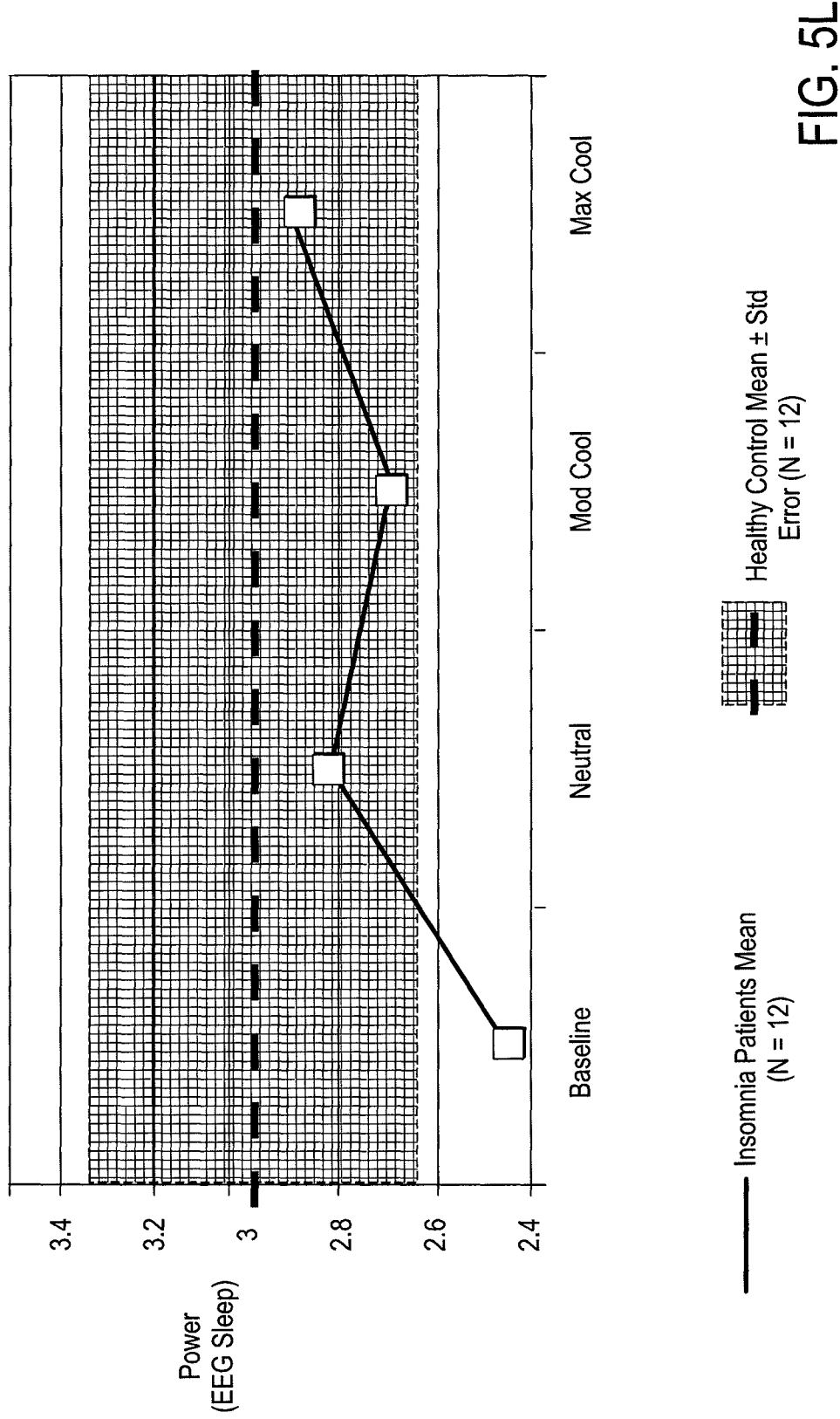
FIG. 5L shows the effect of one variation of a device for applying prefrontal hypothermia on the whole night spectral power in an insomniac patient compared to non-insomniac.

Hypothermic treatment increased the total sleep time (as shown in FIG. 5E) and increased the overall sleep efficiency to within "normal" ranges (FIG. 5F). In addition, hypothermic treatment also shifts EEG sleep stages to deeper stages of sleep, as illustrated in FIGS. 5G-5I. In addition, in these experiments hypothermic treatment also increases slow wave sleep toward healthy levels (FIGS. 5J-5L).

The above effects appear to be dose-dependent, particularly during the early period of application (e.g., sleep onset and early maintenance), with increasing levels of improvement from a neutral temperature to 22° Celsius to 14° Celsius. Thus, depending on the type of sleep desired, it may be possible to vary the temperature in a regulated manner across a night of sleep to alter sleep in a characteristic manner. Varying the temperature may also allow decreased power requirements for the system. Feedback relaying information regarding the type of sleep achieved may also be used to refine the temperature algorithm in a real time manner.

Devices and Systems

Various devices and systems for applying hypothermal treatment to the skin over the prefrontal cortex are described herein. In general these devices include at least one thermal transfer region (e.g., thermal transfer pad) which is configured to cool the skin above the prefrontal cortex.

The thermal transfer region may be any appropriate configuration, particularly those described below. For example, a thermal transfer pad may be shaped to cover the region of the forehead that overlies the frontal cortex of the brain. As described above, the frontal cortex is thought to be important for producing the restorative aspects of sleep based on sleep deprivation studies. Following sleep deprivation, the amount of slow wave sleep, a correlate of the homeostatic function of sleep, is increased in recovery sleep. The increase in slow waves is regionally maximal in the frontal cortex. The frontal cortex has also been shown to show greater reductions in metabolic activity during a recovery night of sleep following sleep deprivation than in relation to regular sleep. Cognitive deficits related to sleep deprivation have also been observed to be in realms thought to be related to frontal cortex function. Brain imaging and EEG sleep research studies described above show that application of a cooling stimulus over the forehead in a shape similar to that of the frontal cortex reduces metabolic activity in the underlying frontal cortex and this is associated with an increase in slow wave sleep, reductions in sleep latency, reductions in wakefulness after sleep onset, an increase in the duration of sleep at night in insomnia patients. Finally insomnia patients have been shown to have increased whole brain and increased frontal cortex metabolism during sleep that is related to their tendency to wake up across a night of sleep.

In some variations, the thermal transfer region may be part of a mask, garment, or other device that directs thermal transfer to the region of the scalp over the frontal cortex to benefit sleep. In some variations the thermal transfer region is limited to cover all or a portion of the frontal cortex. Thus, in some variations the system is configured to limit the region of thermal transfer to the skin region (e.g., forehead).

In some variations the shape of the thermal transfer region (e.g., pad) is custom-shaped to minimize overlap with the hairline of the individual wearing the pad, so as to minimize disruption of hair styles/patterns across a night of sleep. In this arrangement, the shape would maximize the available skin area that is not covered by hair for minimizing interactions with hair styles.

The thermal transfer region may be temperature-regulated by any appropriate mechanism, including air- or water-cooling, as well as solid-state cooling (e.g., Peltier devices), or some combination of these. In variations in which the thermal transfer region is liquid (e.g., water or other liquid coolant) cooled, the system may include a reservoir of cooling fluid that may be located separately from the rest of the device. For example, a mask or thermal applicator (including a thermal transfer region for contacting the patient's skin over the prefrontal cortex region) may be connected by tubing to the reservoir of cooled fluid. The cooled fluid may be pumped through the thermal transfer region to cool the skin and therefore apply hypothermic therapy to the prefrontal cortex. In general, any appropriate method of cooling the thermal transfer region may be used, including non-fluid or non-thermoelectric methods. For example, the thermal transfer region may be cooled by gas, or phase change of liquid/gas, or other chemical endothermic reaction.

In variations including tubing, the tubing may be positioned for optimal comfort during sleep. For example, in some variations, tubes that direct thermal transfer fluids to the mask may be configured to connect away from the patient so that they do not interfere with patient's sleep or risk entanglement with the patient's head or neck as the patient is sleeping with a device on their head. In some variations, the thermal transfer region is connected to the cooled fluid source by inlet/outlet tubing coming out middle of forehead region of the mark or applicator. Individuals tend to sleep on their sides or backs such that the sides of the head and the back of the head can come in contact with the sleeping surface or pillow.

Alternatively, in some variations any inlet/outlet tubing extends from the top of the mask, which may be useful when individuals sleep with their face down. The tubing may be made to swivel, bend, rotate, or flex relative to the mask. For example, a junction between the applicator and the tubing may be a rotating and/or swiveling junction, and may be flexible (particularly compared to more rigid applicator and tubing regions surrounding it).

The thermal transfer region may be connected and held to the patient's head in any appropriate manner. Similarly, any tubing extending from the applicator may be strapped or held so that it extends over top of head and exits middle of head. Another arrangement for connectors and tubing may be over the forehead and out the top of the head, since this part of the head generally does not come in contact with the sleeping surface or pillow. In an alternate configuration, the inlet/outlet tubing coming out over the sides over temples is shaped or configured to course around ears to back of head. Thus in one arrangement, tubing and connectors course over the temples and around the ears to the back of the head. In this arrangement, any tubing and connectors may be made relatively flat to minimize discomfort when the head is lying on them during sleep. The tubing may also be configured so as not to leak or collapse, limiting the heat transfer. Finally, the tubing may be insulated.

The systems described herein may be configured to be worn by the subject every night, and thus may include a washable, disposable, or replaceable skin-contacting region. In some variations the entire applicator is disposable; in other variations only a portion is disposable. For example, the thermal transfer region may be covered by a disposable material or cover that can be replaced nightly with each use. The disposable region (e.g., cover) is generally adapted to transfer heat over all or a portion, so that the thermal transfer region may effectively apply hypothermic therapy to the skin over the frontal cortex. In some variation this cover is configured as a disposable biogel cover.

In some variations the side tubing is integrated with one or more straps for holding the applicator that extend around the back of head. In any of these variations, straps may be utilized to keep the mask on the head and include tubing and connectors integrated into the strap in order to minimize excess tubing/connectors/materials coming off of the mask.

In some variations the system includes a chin strap to help with keeping cap from rising off top of head. In this arrangement, a piece of material comes off the sides of the mask and wraps under the chin of the wearer. The purpose of this is to keep the mask from sliding off the top of the head as may occur during position changes across a night of sleep. In some variations, strap tighteners on front of applicator may be used for easy adjustment and minimal interference with back of head lying on pillow. Any appropriate material may be used for fastening or fasteners, such as Velcro, adhesives, snaps and other types of fasteners, particularly those that minimize any bulk in areas of the mask or straps that might produce discomfort. An example would be having the fasteners in the forehead region where they would not interfere with mask comfort when the head is lying on the sleeping surface.

In some variations the system may include one or more molds for approximating forehead shape in general for similarly sized foreheads and specific forehead moldings for individuals for their unique head size. For example, the materials used for the mask may be specifically molded for the general shape of a head and even more specifically may be molded specifically for each individual who uses the mask to help with sleep. In general the thermal transfer region may have surface that is configured to maximize surface contact of the thermal transfer region to the head surface (skin) to increase the efficiency of heat transfer to the underlying cortex. This can be done by any permanent means such as producing a fixed size mold using a nonmalleable material, or may be done by any means in which some malleable material can be temporarily shaped to the surface features after it has been placed on the head. Examples might include some form of expandable material with a gas or fluid filled cavity that can be inflated, or expanded to conform to the shape of the underlying head, foams, shape-memory materials, or the like.

For example, in some variations the applicator includes one or more injection/vacuum chambers built into cap to increase comfort and increase surface contact for maximizing thermal transfer. Injection or vacuum chambers may be integrated into the mask and can be inflated or deflated to form the mask material to the shape of the head. After placing the mask on the head, either removing liquids or gases from chambers on the underside of the mask or injecting liquids or gases into some outer layer may conform the mask to come in closer approximation to the skin and given the natural curvature of the forehead may create an adhesive seal in which the mask may stay on the head. In one variations the applicator (e.g., mask) has a strapless design using only forehead shape and using injection/vacuum chambers and/or adhesive materials to maintain position of applicator. In this arrangement, some form of temporary adhesion produced by either an adhesive material or some combination of inflation/deflation, or temporary malleability of some material in the mask may serve the purpose of affixing the mask such that additional strappings or coverings to keep the mask in place are not necessary. This strapless arrangement of the applicator may offer increased comfort for some sleeping individuals so that no materials come between the sides and backs of their heads as they lay down for sleep.

In some variations, an integrated eye pad may be included to block out light and/or provide additional cooling of orbital frontal cortex to reduce metabolism in orbital frontal cortex before and during sleep.

In another arrangement, the mask may be constructed such that in addition to covering a region of the head over the frontal cortex, additional materials extend down to cover the orbits over the eyes. This material could serve several functions. First, it may have thermal transfer materials integrated into it so that the orbit is cooled with the intent of cooling the underlying orbitofrontal cortex which may facilitate the metabolic reduction in frontal cortex areas that are conducive for sleep. Another function of this material is to block visual sensory stimuli that could interfere with sleep given the known effects of light on brain arousal. Another function of this material may be to produce a relaxing, stress and anxiety reducing effect caused by the sensation of cooling thermal transfer in this head area. This in itself may facilitate sleep in addition to the effects on underlying brain metabolism. In some variations, the applicator may include thermal insulation around the thermal transfer region to prevent cooling of adjacent region (including the orbits of the eyes), which may be unnecessary and uncomfortable.

In some variations the device may include an integrated ear pad option to either block out noise and/or supply audio input during sleep. For example, the applicator may be configured such that in addition to covering a region of the head over the frontal cortex, additional materials extend down to cover the ears. This material could serve several functions. First, it may have thermal transfer materials integrated into it so that the ear cavities, canals and sinuses are cooled with the intent of cooling the underlying temporal cortex which may facilitate the metabolic reduction in temporal cortex areas that are conducive for sleep. Alternatively or additionally, this material may block auditory sensory stimuli that could interfere with sleep given the known effects of sound on brain arousal and/or may produce a relaxing, stress and anxiety reducing effect caused by the sensation of cooling thermal transfer in this head area. This may facilitate sleep in addition to the effects on underlying brain metabolism.

In some variations the applicator may include (or be configured for use with) an integrated neck pad to provide thermal stimuli to neck arteries to cool the brain before and during sleep to reduce cerebral metabolism before and during sleep and thereby improve sleep quality. Several arteries course through the neck in close approximation to the surface of the neck skin. In another arrangement, the mask would be constructed such that in addition to covering a region of the head over the frontal cortex, additional materials extend down to cover the neck. This material could serve several functions. First, it may have thermal transfer materials integrated into it so that the neck is cooled with the intent of cooling the underlying arteries that supply blood to the brain as a whole which may facilitate a reduction in whole brain metabolism that are conducive for sleep. Another function of this material may be to produce a relaxing, stress and anxiety reducing effect caused by the sensation of cooling thermal transfer in this head area.

In another arrangement, the mask may be constructed such that in addition to covering a region of the head over the frontal cortex, additional materials extend down to cover the sides and back of the neck. This additional material may have thermal transfer materials integrated into it so that the neck is cooled with the intent of cooling the underlying brain regions such as the brainstem, cerebellum and occipital cortex which may facilitate a reduction in metabolism to these regions of the brain that may be conducive for sleep. This material may also produce a relaxing, stress and anxiety reducing effect caused by the sensation of cooling thermal transfer in this head area. This in itself may facilitate sleep in addition to the effects on underlying brain metabolism.

In some variations the system may be configured to provide cooling stimuli to nasal cavities/oropharynx before and during sleep for purpose of cooling/reducing metabolic activity in brainstem/hypothalamus to facilitate sleep. For example, in another arrangement, methods to provide thermal transfer in the area of the nasal cavities/oropharynx in the back of the throat and nasal passages may be applied to cool the underlying brain regions such as the upper brainstem, hypothalamus and orbitofrontal cortex which may facilitate a reduction in metabolism to these regions of the brain that may be conducive for sleep.

In general, the devices and systems may be used combination with (and may be integrated as part of) any other device intended to be worn by a patient during sleeping. For example, devices to treat respiration (e.g., respirators, ventilators, CPAP machines, etc.) may include integrated cooling systems such as those described herein to help enhance sleep, and/or treat sleeping disorders.

As mentioned above, the system described herein may generally include one or more sensors for monitoring either or both the patient and the system components (e.g., thermal transfer region). In some variations the system is configured to measure various parameters on the applicator, including temperature sensors (to measure skin temperature) or electrodes (e.g., to measure EEG parameters) or the like. The system may be configured to provide feedback to the patient/clinician and/or to provide feedback to the system (e.g., the controller) to modify activity of the system.

In addition, in some variations the systems and devices described herein may include additional therapeutic or non-therapeutic modalities which may enhance comfort, relaxation and/or sleep. For example, the systems described herein may include one or more vibratory actions or mechanisms to induce a vibratory/rhythmic/movement sensation on the skin. In one arrangement of the device, a physical sensation may be created that could facilitate sleep and/or produce a relaxing, anxiety or stress reduction purpose that could facilitate sleep and add to the other effects of the device as otherwise noted. For example, physical turbulence in the fluid channels may be permitted or generated. In this arrangement of the device, the direction and movement of fluid within the channels of the thermal transfer pad are configured to have a pleasing, relaxing, calming, stress reducing, massage like effect that could potentiate the positive sensations of the device for the wearer. Similarly, altering pumping pressures of the fluid in a rhythmic manner may be optimized for comfort, soothingness, massaging feeling. In this arrangement of the device, the direction and movement of fluid within the channels of the thermal transfer pad could be altered by various configurations of alternating pressure cycles in the pump, thereby creating a more pleasing, relaxing, calming, stress reducing, massage like effect that could potentiate the positive sensations of the device for the wearer.

In some variations, the system may incorporate a smell or odor stimuli to help enhance comfort and/or effect. For example, the addition of aromas may be subjectively consistent with relaxation/sleep. In this arrangement of the device, the smell of the thermal transfer pad could be altered by various scents, thereby creating a more pleasing, relaxing, calming, stress reducing, effect that could potentiate the positive sensations of the device for the wearer.

As mentioned above, the system may include either direct or indirect modulation of sound when using the device. In general, sounds subjectively consistent with relaxation/sleep may be emitted by the systems (either as part of the applicator or as part of the nearby device, even in variations not including earphones/headphones or the like. In this arrangement of the device, sounds could be added to the thermal transfer pad or (for devices having a remote source of cooling fluid) to a remote unit connecting to the thermal transfer pad, thereby creating a more pleasing, relaxing, calming, stress reducing, effect that could potentiate the positive sensations of the device for the wearer. As mentioned above, the device may include integrated ear pads or plugs with the thermal transfer pad to block out unwanted environmental noises that might interfere with sleep. In another variation of the device the system may be configured to emit white noise, or blocking noises, thereby cancelling out intermittent, variable noises in the environment of the sleeping individual.

Controller

Any of the systems described herein may include a controller for regulating the temperature of the thermal transfer region and thereby providing hypothermic therapy.

In general, the controller (which may be referred to as a hypothermic controller) may control both the applied temperature and the timing (or time-course) of the applied temperature. The controller may be typically configured to apply one or more temperatures to the thermal transfer region for a predetermined amount of time, including following on or more time course for application of cooling. The controller may include a plurality of inputs, including user-selectable inputs (controls for timing, on/off, etc.), as well as feedback (e.g., from the skin surface, or other system feedbacks as described below).

A dose or time course for activation may be referred to as a timeline, or algorithms, of thermal transfer on sleep. For example, in some variations the system in configured to deliver a fixed time course. In one arrangement, a constant thermal transfer rate can be maintained without variation across the period of use. For example, the system may be configured to deliver a dose prior to sleep only. In one arrangement, the thermal transfer applicator could apply treatment for 45 minutes to 1 hour prior to getting in to bed to facilitate the sleep onset process. For example, the system may be configured to cool the thermal transfer region to approximately 14° C. to facilitating sleep onset; based on patient comfort, this temperature may be adjusted to higher temperatures (e.g., up to 30° C.), or it may be a fixed temperature. Similarly, the system may be configured to ramp down to the final temperature (e.g., of 10° C., 14° C., etc.) to allow a subject to acclimate to the temperature). In this application, if effects on only sleep onset were desired, the device could be removed at the time a person got into bed.

In some variations, the system may be configured or adapted for use only when the patient has gone to bed, to operate even after the patient is sleeping. In one arrangement, the applicator could be worn or applied when a person got into bed, and hypothermic therapy applied over a portion or throughout a night of sleep to facilitate the sleep process (including across a night of sleep). In this arrangement, 14° C. or other low temperature (e.g., 10° C.) may be maximally effective, and higher temperatures less effective, in facilitating deeper sleep especially in the first half of the night, with less significant effects later in the night.

In some variations the system may be configured to provide hypothermal therapy both before desired sleep time (GNT) and after initially falling asleep. For example, in one arrangement, the thermal transfer pad could be applied 45 minutes to 1 hour prior to getting in to bed to facilitate the sleep onset process and left on throughout a night of sleep to facilitate the sleep process across a night of sleep. Thus, the controller may be configured to initially apply a sleep onset time course (e.g., ramping to a sleep-onset temperature such as about 14° C., and maintaining that temperature for a predetermined time period, such as 30 min-1 hr.), and then transition to a sleep maintenance time course (e.g., maintaining the temperature at a relatively low temperature such as about 14° C. for the first 2-4 hours of sleep or for the rest of the night, or gradually increasing the temperature to a higher level thereafter). The maintenance time course may maintain deeper sleep across the night with lesser degrees of facilitation in higher temperatures up to 30° C.

Thus, in some variations the time course is constant, while in other variations, the time course is variable (including changes in the temperature over the sleep period). For example, in one arrangement, a variable thermal transfer rate with defined changes can be delivered across the period of use. While changes in device temperature are felt immediately at the skin surface, there is a delay between the time a cooling stimulus is applied to the head surface and the time cooling is achieved in the underlying cortex. Variable time course algorithms, therefore, may include different delays built in between the time of application and the time of the desired effect on either the temperature sensation at the skin surface or on the temperature of the underlying brain and resulting effects on brain metabolism. In one arrangement a delay of approximately 30 minutes may be built in to the systems variable time course algorithms.

In some variations the systems described herein are configured for use prior to falling asleep (which may be referred to as pre-cooling devices or systems). Thus, the device and method of operation may be configured specifically for being worn to increase drowsiness or decrease the latency to sleep of a patient. The device may be adapted by including timing controls adapted for the pre-sleep cooling described herein. In some variations the system may be configured to differentiate between long and short sleep periods; for example, the system may be configured to facilitate "napping" (short sleeps) or longer-duration sleeping. In some variations the system includes controls (and timers) for selecting sleep duration, and may alter the applied hypothermic therapy on the basis of the control. In the napping mode the system may provide an initially high level of cooling (e.g., to between 10° C. and 18° C.) and shift after a first time period to a higher temperature (e.g., 24° C., or some temperature between about 20-28° C.) or shift to a thermally "neutral" temperature (e.g., about 30° C.). In some variations, the system or device is configured as a "napping" device as opposed to a 6-8 hour sleep period device.

As mentioned above, in some variations the system includes one or more ramping time courses. For example, the thermal transfer region could be applied at a neutral temperature of approximately 30° C. at 45 minutes to 1 hour prior to getting in to bed, and then the temperature ramped down to approximately 14° C. (e.g., between 10 and 25° C.) over a matter of minutes, while adjusting the rate of ramping to skin surface comfort levels, to facilitate the sleep onset process. Similarly, any set temperature could be achieved by first applying the device at a neutral comfortable skin temperature then ramping the temperature over time to achieve the desired final endpoint temperature.

In some variations the time course may be varied based on either predetermined values or based on feedback. For example, a sleep maintenance time course may be applied that may include varying the time course of thermal transfer in coordination with the probability of NREM and REM sleep stage occurrences. Brain temperature as well as brain blood flow and brain metabolism vary in characteristic ways across a night of sleep and is dependent on the stage of sleep an individual may be in as well as the duration of time from the beginning of sleep. NREM sleep stages include lighter stage 1 sleep, deeper stage 2 sleep and deepest stages slow wave sleep with slow wave sleep predominating in the first half of the night. REM sleep occurs cyclically across a night, every 60-90 minutes with progressively longer and more intense REM periods occurring in the latter parts of the night. Brain temperature, blood flow and metabolism tend to lessen in deeper NREM sleep and increases in REM sleep. The degree to which these changes occur are thought to be functionally important for sleep. The cooling device may therefore facilitate the deepening of NREM sleep by applying a time course that mimics or follows the time course of a normal sleep cycle. This may result in reducing metabolic activity in the frontal cortex with consequent increases in slow wave sleep.

In one arrangement of a variable thermal transfer time course, therefore, the maximal cooling may be concentrated earlier in the night when slow wave sleep tends to be maximal, with less significant cooling towards the end of the night when REM sleep and natural brain warming would be occurring. One algorithm (e.g., time course) may therefore include a thermal transfer at the coolest temperature tolerated without discomfort (e.g., between about 10° C. and about 14° C. at the beginning of the night and ramping to a neutral 30° C. temperature by the end of a night's sleep). This ramping could be linear across the night, or could have a curvilinear component where maximal cooling is concentrated in periods where slow wave sleep has a high probability of occurring as revealed by normative curves of slow wave sleep production across the night.

It is known that some disorders, such as depression for example, have characteristic alterations in REM sleep. The dose-ranging research study above demonstrates that altering the temperature of the thermal transfer mask has predictable effects on the occurrence of REM sleep. One algorithm, therefore, may include a variable thermal transfer across the night that is intended to target the occurrence of REM sleep in a therapeutic manner. In depression, for example, where REM sleep duration and intensity seem to be more highly concentrated in the first third of the night, use of a time course having a temperature of the coolest tolerable temperature (e.g., 14° C.) over this period would be expected to inhibit abnormal REM sleep production whereas the use of more neutral temperatures in the latter half of the night would be expected to lead to more normal REM sleep production in that part of the night.

Similarly, alterations in REM and NREM sleep can occur in a variety of neuropsychiatric disorders. The general principle of altering the temperature of the thermal transfer region of the applicator to facilitate or diminish discrete aspects of deep NREM sleep or REM sleep that are directly related to the specific disorder would be expected to have therapeutic utility specific to the disorder.

As mentioned briefly above, the system may include feedback to the controller to regulate the applied hypothermic therapy. Surprisingly, altering the applied hypothermic therapy has a predictable effect on sleep physiology, as described above. It may be possible, therefore, to measure the changes in sleep physiology and incorporate them into a feedback loop that then results in changes in the thermal transfer. In this manner, the amount of thermal transfer applied can be adjusted in real time to achieve some desired physiological effect.

In one arrangement a variable thermal transfer rate with defined changes can be delivered across the period of use with the changes linked to feedback from changes in the physiology of the body across a period of use. Physiological measures may be monitored and thermal transfer adjusted in real time according to the level of the physiological measure. For example, the system may include feedback based on the presence or absence of REM or NREM sleep as assessed by any method of REM/NREM sleep assessment, such as EEG frequency, Heart Rate Variability, Muscle Tone or other mechanism. Thus, the device or system may include one or more sensors (electrodes, etc.) that provide at least some indication of sleep cycle, this information may be fed or monitored by the controller, which may modulate the applied dose based on the detected REM/NREM status. The perceived status may be compared to an expected or desired status, which may alter the applied hypothermic therapy.

In some variations, the system may also or alternatively monitor and/or react to the depth of slow wave sleep, as measured by EEG wave analysis or other mechanism. Similarly, the system may monitor and/or respond to the degree of autonomic arousal as measured by HR variability or other mechanism. Other examples of characteristic that may be (separately or in combination) monitored and/or feed back into the system to modulate the applied hypothermy is galvanic skin response, skin temperature, eye motion during sleeping, and gross body motion during sleeping. For example, skin temperature may be measured either at the skin on the head underneath the device, or on skin at some other portion of the head not underneath the device, or peripheral skin temperature, or core body temperature (measured internally or by some external means) or some combined measure assessing thermoregulation of the head and periphery, or core body to peripheral temperature measure. Eye motion or body motion may be monitored optically or through one or more motion or position sensors (including accelerometers).

In many of the systems and devices described herein the control may be adjusted by the subject wearing the device (and/or by a physician or other professional). In some variations, the person wearing the device can modify the thermal transfer rate across the period of use with the changes linked to subjective feedback. For example, a control on the device may allow the person wearing the device to adjust the temperature according to their immediate comfort and treatment needs, either up or down some small increments.

In another arrangement, an individual can set their go to bed times and desired get out of bed times, then a preprogrammed algorithm is input to start and stop at those times and provide the incremental adjustments to occur on a relative basis over this time period. These automated time calculations could be implemented for any variable schedule of thermal transfer rates across any defined period of time.

In general, the temperature of the skin beneath the applicator (e.g., the thermal transfer region of the applicator) may also be monitored. Although the system and/or device may apply a predetermined temperature to the skin through the applicator, the temperature of the skin does not necessarily become cooled to this temperature, but is typically higher. In some variations skin temperature beneath the thermal transfer region may be monitored and/or fed back into the controller to regulate the applied temperature. As mentioned above, the thermal contact between the skin and the applicator may be optimized or regulated. For example, the materials forming the applicator (and particularly the thermal transfer region) may be optimized or otherwise selected to determine the temperature applied. In one variation the lining of the transfer pad that comes in contact with the skin is a hydrogel allowing for increased surface area contact and increased thermal transfer characteristics. In another arrangement, this lining is combined with dermatologic products that can be rejuvenating for the skin when in contact over the course of a night. In another arrangement, an inner lining can be refreshed on a nightly or less frequent basis that can benefit the skin when applied over the night of sleep.

During the daytime, when not in use, the cooling chamber, any tubing and headgear may be stored until the next night's use. In some variations the device is self-contained (e.g., battery powered, particularly for solid-state devices). Thus the device may be re-charged when not in use. In one arrangement, the equipment can all be contained in a storage box for an attractive appearance, which may also be functional (e.g., recharging, sanitizing, protection, etc.). In variations including tubing, the tubing can automatically recoil into a storage region (e.g., box) when not in use for maintaining an attractive appearance. In some variations, the applicator is stored with antiseptic materials and/or in an environment that provide for antiseptic cleaning and storage to minimize the potential for growth of organisms that may be harmful to the wearer.

Because the device is intended for use at night, the controls may be optimized for use in low lighting. A subject using the device may have to interact with the device at night when illumination would be expected to be low, thus in some variations, the device or system includes control features that the individual needs to interact with would become lit only when an individual comes in close contact with the device.

In another arrangement of the device, control features may be made of an illumination level that minimally interferes with sleep. In another arrangement of the device, control features may be voice activated. In another arrangement of the device, control features have physical features that can be identified by touch and differentiate themselves from other parts of the device to let an individual know in the dark where the control buttons are located.

In general, it may be particularly desirable to include one or more features that record (and/or analyze) use of the device or system. For example, in the clinical management of a patient, a healthcare provider may want to know certain parameters of the patient and/or device over multiple nights of use such that care can be optimized. In some variations, the system or device includes memory (e.g., a memory card or memory chip) that may automatically record certain parameters and store them for later display by the healthcare provider. For example, the operation of the controller may be recorded.

In monitoring their own care, a device user may want to know certain parameters of the patient and/or device over multiple nights of use such that care can be optimized. In one arrangement of the device, therefore, memory may automatically record certain parameters and store them for later display. This information could be transferred to a healthcare provider's office or some other central database via the phone or internet or some wireless technology where someone could review the information and provide recommended adjustments in the treatment accordingly. Examples of information that may be stored could include, but would not be limited to: temperature of the device; skin temperature; core body temperature; measures of autonomic variability; depth of sleep as assessed by NREM sleep, EEG power in discrete frequency bands, REM sleep or other sleep staging; periods of activity and/or wakefulness across the night; subjective measures of sleep depth/comfort/satisfaction; and sleep duration.

In some variations this information may be automatically collected, while in other variations it may be entered by the subject or a third party.

Indications and Methods for Operation

As mentioned above, the systems and devices described herein may generally be used to treat sleeping disorders. In particular, these systems and methods may be used to treat insomnia. Thus, the systems and devices described herein may be used to facilitate sleep. For example, the systems and devices described herein may be used to decrease sleep latency (e.g., the time to fall asleep), and/or increase sleep duration.

In operation, a method of modulating sleep (e.g., increasing sleep duration) may include the steps of positioning and/or securing the thermal transfer region on the forehead or scalp of the subject (who may also be referred to as a patient) in the region over the area of the frontal cortex and (in some variations) related areas. The system or device may then apply hypothermic therapy (e.g., cooling) to the skin to reduce metabolic activity in the underlying frontal cortex and related areas thereby facilitating or modulating sleep.

As discussed above, in some variations the systems and device may be applied prior to sleep to aid in sleep onset. For example, the system may include the step of applying the thermal transfer region in contact with the skin over the prefrontal region for a time period (e.g., 15 minutes, 30 minutes, 45 minutes, 60 minutes, etc.) before a desired good night time (GNT, the desired time to fall asleep). Regional hypothermia may be used alone or in conjunction with other relaxation and/or pre-sleep therapies to enhance sleepiness and decrease the latency to sleep.

In some variations, the method of use may include (or be limited to) a method of increasing slow wave sleep, a method of increasing sleep maintenance, a method of reducing awakenings, and/or a method of increasing the time spent asleep across the night. In general, each of these methods may include the steps of placing the applicator (including the thermal transfer region) in contact to transfer thermal energy from the subject's skin above the prefrontal cortex. Thereafter, the system may execute a treatment regime including cooling to a temperature such as the lowest temperature that may be tolerated by the subject without resulting in discomfort (including arousals) such as pain or tissue damage. Typically this temperature may be between about 10° C. and about 25° C. (e.g., 11° C., 12° C., 13° C., 14° C., 15° C., 16° C., etc.). The temperature may be lowered slowly (e.g., in a ramp, such a linear ramp) or more quickly. The treatment regime may hold this first target temperature for a first time period (which in some cases may be a predetermined time period such as 1 hour, 2 hours, 3 hours, 4 hours, 5 hours, etc.) or it may be determined based on patient feedback and/or control setting. Thereafter the temperature may be increased and/or decreased in one or a series of dosage settings. In some variations the dosage follows a predetermined treatment parameter that increases the temperature from an initially low value to a slightly higher temperature later in the evening to help maintain sleep.

Any of the methods described herein may be used to treat insomniacs, however these methods may also be used to generally improve healthy sleep, even in non-insomniac subjects. In particular, these methods, devices and systems may be used to improve sleep in individuals who experience sleeplessness.

Further, the systems and devices described herein may be used as part of a method to treat and improve sleep in individuals with neuropsychiatric disorders such as, but not limited to, depression, mood disorders, anxiety disorders, substance abuse, post-traumatic stress disorder, psychotic disorders, manic-depressive illness and personality disorders and any neuropsychiatric patient who experiences sleeplessness.

Sleep reduction and disruption is known to be associated as a co-morbidity in a number of disorders, and the devices and systems described herein may be used to help alleviate such disorders, in part by helping modulate and enhance sleep. For example, the devices and systems described herein may be used to improve sleep in patients with pain, including chronic pain, and headaches, including migraine headaches, and cardiac, endocrinologic, and pulmonary disorders, and tinnitus.

The systems and devices may also be used in a waking subject to enhance relaxation and improve waking function.

The treatment regime may be similar or different from the treatment regimens used to enhance sleepiness and/or prolong sleep. For example, the devices and systems described herein may be used to improve waking function by reducing metabolic activity in the frontal cortex during waking, including: reducing the experience and distress of tinnitus and chronic pain; increasing mental and cognitive focus; producing a subjective feeling of relaxation; producing a subjective feeling of soothing; producing a subjective feeling of comfort; producing a subjective feeling of stress reduction; improving mood in patients with depression; reducing fears, anxieties in patients with anxiety disorders; reducing distracting thoughts; and/or reducing obsessive thoughts, and behaviors.

In such non-sleeping variations, it may be useful to allow subject-control of the system, including subject control of the duration and level of cooling applied. In some variations predetermined settings for different applications may be included as part of the system.

Another application of the systems and devices described herein includes thermoregulation and fever reduction. The devices and systems may be used to reduce generalized fever and could be utilized for fever control, particularly in individuals with elevated core body temperatures from a variety of causes, including, but not limited to, infection. In some variations the systems and devices described herein may be used or configured for use in conjunction with (or integrated into) a system for light therapy for Circadian Rhythm Disorders ("CRD").

In addition, the devices and systems described herein may also be used to alter circadian rhythms and could therefore be applicable for use in circadian rhythm disorders such as shift work disorder, phase advance and phase delay circadian rhythm disorders.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating a migraine by non-invasively applying hypothermal therapy to a subject's frontal cortex, the method comprising:
   positioning an applicator comprising a thermal transfer region in communication with the subject's skin over the subject's prefrontal cortex;
   passing cooled fluid through the applicator so that the thermal transfer region is cooled to a first temperature between about 10° C. and about 25° C.;
   maintaining the first temperature for a first time period extending at least 15 minutes.

2. The method of claim 1, herein the method of treating the migraine further comprises a method of treating a migraine so that the subject may sleep.

3. The method of claim 1, further comprising connecting the applicator to a fluid source.

4. The method of claim 1, further comprising maintaining contact between the subject's skin over the subject's prefrontal cortex and the thermal transfer region so that the metabolism in the prefrontal cortex is slowed.

5. The method of claim 1, wherein positioning the applicator comprises securing the applicator over just the subject's forehead region.

6. The method of claim 1, wherein passing the cooled fluid through the applicator comprises ramping the temperature of the thermal transfer region from ambient temperature to the first temperature over at least five minutes.

7. The method of claim 1, wherein maintaining the first temperature comprises maintaining the first temperature for at least 30 minutes.

8. The method of claim 1, wherein maintaining the first temperature comprises maintaining the first temperature for at least one hour.

9. The method of claim 1, wherein the treating the migraine comprises reducing sleep onset in the subject.

10. The method of claim 1, wherein the method of treating the migraine further comprises a method of preventing the migraine.

11. A method of treating a migraine by non-invasively applying hypothermal therapy to a subject's frontal cortex so that the subject falls asleep faster, the method comprising:
    coupling an applicator comprising a thermal transfer region to a fluid source;
    positioning the thermal transfer region in communication with the subject's skin over at least a portion of the subject's frontal cortex, prefrontal cortex or frontal and prefrontal cortex;
    maintaining the applicator temperature by pumping fluid from the fluid source through the thermal transfer region; and
    maintaining the temperature for a time period extending at least 15 minutes.

12. The method of claim 11, further comprising maintaining contact between the subject's skin over the subject's frontal cortex, prefrontal cortex or frontal and prefrontal cortex and the thermal transfer region so that the metabolism in the cortex is slowed.

13. The method of claim 11, wherein positioning the applicator comprises securing the applicator in position.

14. The method of claim 11, wherein coupling the applicator comprises coupling the thermal transfer region to the fluid source via tubing coming out from a middle of a forehead region of the applicator.

15. The method of claim 11, wherein positioning the applicator comprises securing the applicator over just the subject's forehead region.

16. The method of claim 11, wherein maintaining the applicator temperature comprises maintaining the temperature between about 10° C. and about 25° C.

17. The method of claim 11, wherein maintaining the temperature comprises maintaining the temperature for at least 30 minutes.

18. The method of claim 11, wherein maintaining the temperature comprises maintaining the temperature for at least one hour.

19. The method of claim 11, wherein pumping fluid from the fluid source through the thermal transfer region comprises altering pumping pressures of the fluid in a rhythmic manner.

20. A method of treating a migraine by non-invasively applying hypothermal therapy to a subject's frontal cortex so that the subject falls asleep faster, the method comprising:
coupling an applicator comprising a thermal transfer region to a fluid source, wherein the thermal transfer region comprises one or more channels, through which fluid may be moved;
positioning the thermal transfer region in communication with the subject's skin over at least a portion of the subject's frontal cortex, prefrontal cortex or frontal and prefrontal cortex;
maintaining the applicator temperature by pumping fluid from the fluid source through the thermal transfer region, wherein the fluid passes into and out of the thermal transfer region via tubing coming out from a middle of a forehead region of the applicator; and
maintaining the temperature for a time period extending at least 15 minutes.

* * * * *